(12) United States Patent
Kojima

(10) Patent No.: US 12,059,133 B2
(45) Date of Patent: Aug. 13, 2024

(54) LIGHT SOURCE APPARATUS, MEDICAL OBSERVATION SYSTEM, ADJUSTMENT APPARATUS, ILLUMINATION METHOD, ADJUSTMENT METHOD, AND PROGRAM

(71) Applicant: Sony Olympus Medical Solutions Inc., Tokyo (JP)

(72) Inventor: Koji Kojima, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 488 days.

(21) Appl. No.: 17/310,221

(22) PCT Filed: Jan. 17, 2020

(86) PCT No.: PCT/JP2020/001608
§ 371 (c)(1),
(2) Date: Jul. 27, 2021

(87) PCT Pub. No.: WO2020/170669
PCT Pub. Date: Aug. 27, 2020

(65) Prior Publication Data
US 2022/0133140 A1 May 5, 2022

(30) Foreign Application Priority Data
Feb. 18, 2019 (JP) .................. 2019-026889

(51) Int. Cl.
*A61B 1/06* (2006.01)
*A61B 1/00* (2006.01)
(52) U.S. Cl.
CPC ........ *A61B 1/0684* (2013.01); *A61B 1/00057* (2013.01); *A61B 1/0655* (2022.02); *A61B 1/0669* (2013.01)

(58) Field of Classification Search
CPC . A61B 1/0684; A61B 1/0655; A61B 1/00057; A61B 1/0669
(Continued)

(56) References Cited

U.S. PATENT DOCUMENTS

| 2011/0128607 A1 | 6/2011 | Ishii |
| 2018/0140173 A1* | 5/2018 | Nishio ................ A61B 1/0655 |
| 2018/0343725 A1 | 11/2018 | Nagata |

FOREIGN PATENT DOCUMENTS

| JP | 2011-101771 A | 5/2011 |
| JP | 2015-530893 A | 10/2015 |

(Continued)

OTHER PUBLICATIONS

International Search Report and Written Opinion mailed on Mar. 31, 2020, received for PCT Application PCT/JP2020/001608, Filed on Jan. 17, 2020, 8 pages including English Translation.

*Primary Examiner* — William Choi
(74) *Attorney, Agent, or Firm* — XSENSUS LLP

(57) ABSTRACT

A light source apparatus, a medical observation system, an adjustment apparatus, an illumination method, an adjustment method, and a program that enable performing light modulation on a semiconductor light source through PWM control and current control without the necessary of a complicated work are provided. A light source apparatus 3 includes a first light source section 31 that emits a first light, a second light source section 32 that emits a second light, and a light source control section 33 that controls each of a pulse emission time and a pulse emission intensity of the first light and performs a control that changes one of a pulse emission time and a pulse emission intensity of the second light with the other one of the pulse emission time and the pulse emission intensity of the second light fixed.

14 Claims, 13 Drawing Sheets

(58) Field of Classification Search
USPC .......................................................... 359/290
See application file for complete search history.

(56) References Cited

FOREIGN PATENT DOCUMENTS

| | | |
|---|---|---|
| JP | 5789348 B2 | 10/2015 |
| JP | 2017-136396 A | 8/2017 |
| JP | 6173002 B2 | 8/2017 |
| WO | WO-2016031359 A1 | 3/2016 |
| WO | WO-2018198507 A1 | 11/2018 |

* cited by examiner

FIG.13

| | CURRENT VALUE | EMISSION TIME | EMISSION INTENSITY |
|---|---|---|---|
| FIRST LIGHT SOURCE SECTION | $I_{min}$ | $T_{min}$ | $XXX_{min}$ |
| | $I_{min}$ | $T_{min+1}$ | $XXX$ |
| | ⋮ | ⋮ | ⋮ |
| | $I_{min}$ | $T_{max}$ | $XXX$ |
| | $I_{min+1}$ | $T_{max}$ | $XXX$ |
| | ⋮ | ⋮ | ⋮ |
| | $I_{max}$ | $T_{max}$ | $XXX_{max}$ |
| SECOND LIGHT SOURCE SECTION | $I_{max}$ | $T_{min}$ | $XXX_{min}$ |
| | $I_{max}$ | $T_{min+1}$ | $XXX$ |
| | ⋮ | ⋮ | ⋮ |
| | $I_{max}$ | $T_{max}$ | $XXX_{max}$ |

G1

LIGHT SOURCE APPARATUS, MEDICAL OBSERVATION SYSTEM, ADJUSTMENT APPARATUS, ILLUMINATION METHOD, ADJUSTMENT METHOD, AND PROGRAM

CROSS-REFERENCE TO RELATED APPLICATIONS

The present application is based on PCT filing PCT/JP2020/001608, filed Jan. 17, 2020, which claims priority to JP 2019-026889, filed Feb. 18, 2019, the entire contents of each are incorporated herein by reference.

TECHNICAL FIELD

The present disclosure relates to a light source apparatus that irradiates an object with light, a medical observation system, an adjustment apparatus, an illumination method, an adjustment method, and a program.

BACKGROUND ART

There has been known a technology for endoscopes, in which a semiconductor light source that irradiates an object with light, such as an LED light source or a semiconductor laser device, is subjected to PWM control that changes a duty ratio of a drive pulse and current control that changes a current in the semiconductor light source, thereby performing light modulation of the semiconductor light source (for example, see PTL 1). In this technology, lights in wavelength bands different from each other are subjected to the PWM control and the current control on a frame-by-frame basis, thereby performing normal observation with white light or special observation with a narrow band light (Narrow Band Imaging: NBI).

CITATION LIST

Patent Literature

[PTL 1]
Japanese Patent No. 5789348

SUMMARY

Technical Problem

In this regard, semiconductor light sources vary in manufacturing process and performance. Accordingly, performing current control and PWM control with a high accuracy necessitates an adjustment work, which includes detecting data regarding maximum current value and minimum current value for causing light emission, a correlation function between current and intensity of outgoing light, etc., during an inspection process before shipping of an endoscope light source apparatus and storing a result of the detection in a ROM (Read Only Memory) or the like. A light source apparatus including a typical semiconductor light source thus requires performing, in a case where all the light sources are to be subjected to light modulation by the current control, the adjustment work on all the semiconductor light sources, which disadvantageously complicates the work.

The present disclosure has been made in view of the above and an object thereof is to provide a light source apparatus, a medical observation system, an adjustment apparatus, an illumination method, an adjustment method, and a program that enable light modulation of a semiconductor light source through PWM control and current control without the necessary of a complicated work.

Solution to Problem

To solve the above-described problem to achieve the object, a light source apparatus according to the present disclosure includes a first light source section that is capable of pulse emission and emits a first light with which an object is to be irradiated, a second light source section that is capable of pulse emission and emits a second light with which the object is to be irradiated, and a light source control section that controls each of a pulse emission time and a pulse emission intensity of the first light and performs a control that changes one of a pulse emission time and a pulse emission intensity of the second light with the other one of the pulse emission time and the pulse emission intensity of the second light fixed. In the first light source section, a brightness of a captured image corresponding to an imaging signal generated as a result of an imaging device receiving light from the object irradiated with the first light with the pulse emission time and the pulse emission intensity of the first light maximized is higher than a brightness of a captured image corresponding to an imaging signal generated as a result of the imaging device receiving light from the object irradiated with the second light with the pulse emission time and the pulse emission intensity of the second light maximized.

Further, as described in above-disclosure, in the light source apparatus according to the present disclosure, the first light source section generates, as the first light, light enabling white-color observation, and the second light source section generates, as the second light, light that excites a fluorescent substance.

Further, as described in above-disclosure, in the light source apparatus according to the present disclosure, the light source control section performs a control that causes the first light source section and the second light source section to alternately emit the light and performs a control that changes the pulse emission time with the pulse emission intensity of the second light fixed during emission from the second light source section.

Further, a medical observation system according to the present disclosure includes the light source apparatus of the above-described disclosure, an imaging device that receives light from the object and generates an imaging signal, and an image processing section that generates, from the imaging signal generated by the imaging device, a display image to be displayed on a display section.

Further, an adjustment apparatus according to the present disclosure optically capable of coupling to the light source apparatus of the above-described disclosure and includes a measurement section that is able to measure an emission intensity of each of the first light and the second light, and a control section that causes the first light source section or the second light source section to emit light at a predetermined current value. The control section generates, based on a difference between a result of measurement by the measurement section and a preset emission intensity, calibration data in which an adjusted value provided by adjusting the current value and the preset emission intensity are associated with each other, and causes a memory of the light source apparatus to record the calibration data.

Further, an illumination method according to the present disclosure is to be performed by a light source apparatus. The light source apparatus includes a first light source section that is capable of pulse emission and emits a first light with which an object is to be irradiated, and a second light source section that is capable of pulse emission and emits a second light with which the object is to be irradiated. A brightness of a captured image corresponding to an imaging signal generated as a result of an imaging device receiving light from the object irradiated with the first light with a pulse emission time and a pulse emission intensity of the first light maximized is higher than a brightness of a captured image corresponding to an imaging signal generated as a result of the imaging device receiving light from the object irradiated with the second light with a pulse emission time and a pulse emission intensity of the second light maximized. The illumination method includes controlling each of the pulse emission time and the pulse emission intensity of the first light, and changing one of the pulse emission time and the pulse emission intensity of the second light with the other one of the pulse emission time and the pulse emission intensity of the second light fixed.

Further, an adjustment method according to the present disclosure is to be performed by an adjustment apparatus optically coupled to a light source apparatus. The light source apparatus includes a first light source section that is capable of pulse emission and emits a first light with which an object is to be irradiated, and a second light source section that is capable of pulse emission and emits a second light with which the object is to be irradiated. A brightness of a captured image corresponding to an imaging signal generated as a result of an imaging device receiving light from the object irradiated with the first light with a pulse emission time and a pulse emission intensity of the first light maximized is higher than a brightness of a captured image corresponding to an imaging signal generated as a result of the imaging device receiving light from the object irradiated with the second light with a pulse emission time and a pulse emission intensity of the second light maximized. The adjustment method includes measuring an emission intensity of each of the first light and the second light, causing the first light source section or the second light source section to emit light at a predetermined current value, generating, based on a difference between a result of the measuring of the emission intensity of each of the first light and the second light and a preset emission intensity, calibration data in which an adjusted value provided by adjusting the current value and the preset emission intensity are associated with each other, and causing a memory of the light source apparatus to record the calibration data.

Further, a program according to the present disclosure is to be executed by a light source apparatus. The light source apparatus includes a first light source section that is capable of pulse emission and emits a first light with which an object is to be irradiated, and a second light source section that is capable of pulse emission and emits a second light with which the object is to be irradiated. A brightness of a captured image corresponding to an imaging signal generated as a result of an imaging device receiving light from the object irradiated with the first light with a pulse emission time and a pulse emission intensity of the first light maximized is higher than a brightness of a captured image corresponding to an imaging signal generated as a result of the imaging device receiving light from the object irradiated with the second light with a pulse emission time and a pulse emission intensity of the second light maximized. The program includes controlling each of the pulse emission time and the pulse emission intensity of the first light, and changing one of the pulse emission time and the pulse emission intensity of the second light with the other one of the pulse emission time and the pulse emission intensity of the second light fixed.

Further, a program according to the present disclosure is to be executed by an adjustment apparatus optically coupled to a light source apparatus. The light source apparatus includes a first light source section that is capable of pulse emission and emits a first light with which an object is to be irradiated, and a second light source section that is capable of pulse emission and emits a second light with which the object is to be irradiated. A brightness of a captured image corresponding to an imaging signal generated as a result of an imaging device receiving light from the object irradiated with the first light with a pulse emission time and a pulse emission intensity of the first light maximized is higher than a brightness of a captured image corresponding to an imaging signal generated as a result of the imaging device receiving light from the object irradiated with the second light with a pulse emission time and a pulse emission intensity of the second light maximized. The program includes measuring an emission intensity of each of the first light and the second light, causing the first light source section or the second light source section to emit light at a predetermined current value, generating, based on a difference between a result of the measuring of the emission intensity of each of the first light and the second light and a preset emission intensity, calibration data in which an adjusted value provided by adjusting the current value and the preset emission intensity are associated with each other, and causing a memory of the light source apparatus to record the calibration data.

Advantageous Effect of Invention

The present disclosure is effective in enabling light modulation of a semiconductor light source through PWM control and current control without the necessity of performing a complicated work.

BRIEF DESCRIPTION OF DRAWINGS

FIG. 13 schematically illustrates an example of calibration data generated by the adjustment apparatus according to Embodiment 4 with use of the light source apparatus.

DESCRIPTION OF EMBODIMENTS

Figure 1:
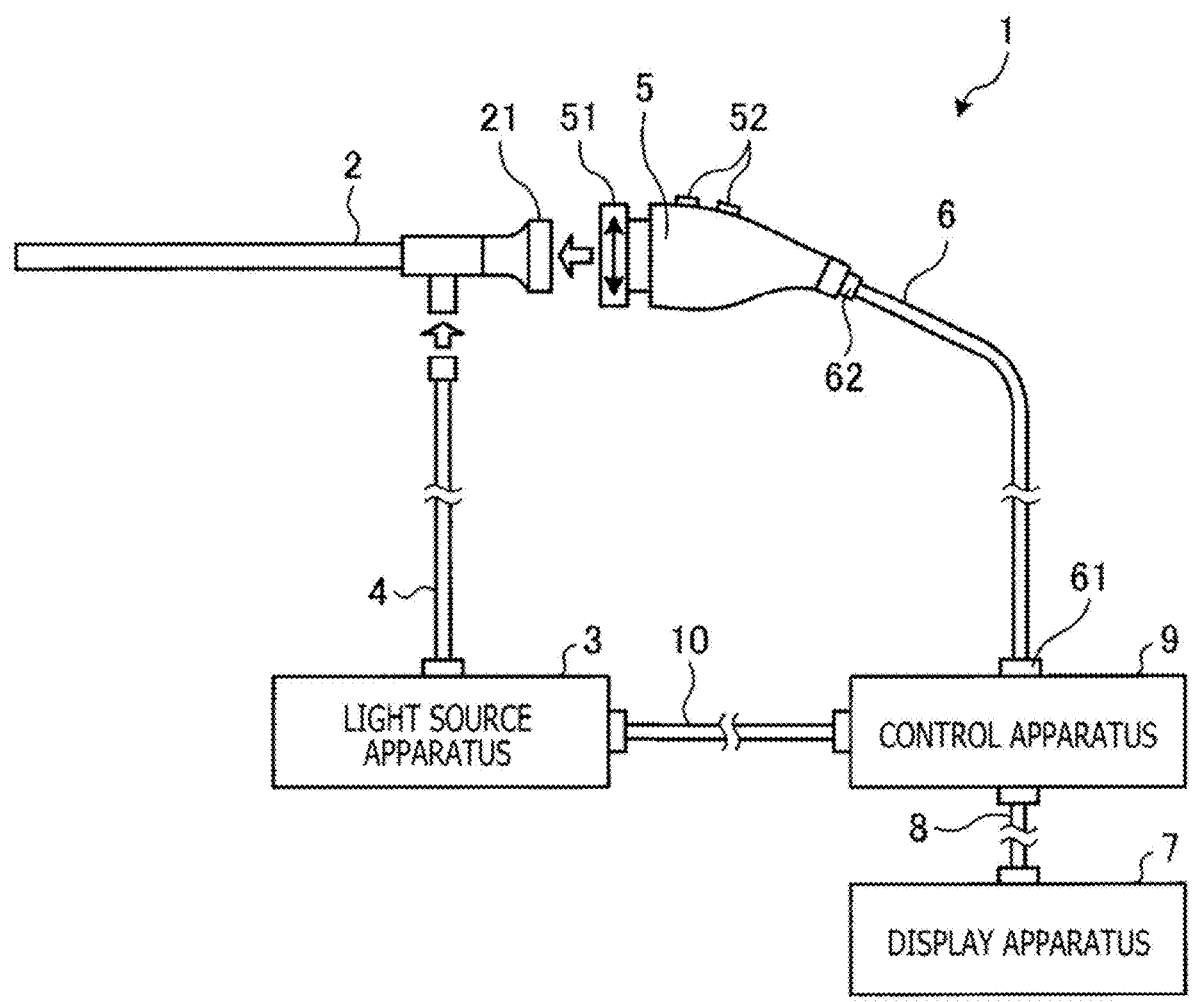
FIG. 1 illustrates a schematic configuration of an endoscope system according to Embodiment 1.

A detailed description will be made below on modes for carrying out the present disclosure (hereinafter, referred to as "embodiments") with reference to the drawings. It should be noted that the present disclosure is not limited to the following embodiments. In addition, the drawings referred to in the following description merely schematically illustrate shapes, sizes, and positional relations in a manner sufficient to make the contents of the present disclosure understandable. In other words, the present disclosure is not limited only to the shapes, the sizes, and the positional relations illustrated by way of examples in the drawings. Further, the description is made with the same reference signs used to refer to the same sections in the illustration of the drawings. Moreover, an endoscope system is described as an example of a medical observation system according to the present disclosure. Furthermore, the description is made with the same reference signs used to refer to the same sections in the illustration of the drawings.

Embodiment 1

[Schematic Configuration of Endoscope System]

FIG. 1 illustrates a schematic configuration of an endoscope system according to Embodiment 1.

An endoscope system 1 illustrated in FIG. 1 is an apparatus usable in a medical field and that is to be inserted inside (into a body) of an object, e.g., a living body such as a human being or an animal, displaying a captured image of the inside such that the object is observed. It should be noted that a rigid endoscope system including a rigid scope (an insertion section 2) illustrated in FIG. 1 will be described as the endoscope system 1 in Embodiment 1; however, this is not limiting and, for example, a flexible endoscope system is also acceptable.

The endoscope system 1 illustrated in FIG. 1 includes the insertion section 2 (an endoscope), a light source apparatus 3, a light guide 4, a camera head 5 (an endoscope imaging apparatus), a first transmission cable 6, a display apparatus 7, a second transmission cable 8, a control apparatus 9, and a third transmission cable 10.

The insertion section 2, which is rigid or at least partially flexible and is in an elongated shape, is to be inserted into an object such as a patient. An optical system including one or plural lenses and that combines an observation image is provided in the insertion section 2.

One end of the light guide 4 is coupled to the light source apparatus 3. The light source apparatus 3 outputs (supplies) light for illuminating the inside of the object to the one end of the light guide 4, under the control of the control apparatus 9. The light source apparatus 3 includes a semiconductor laser device such as an LD (Laser Diode). The light source apparatus 3 and the control apparatus 9 may be configured to individually perform communication as illustrated in FIG. 1 or may be integrally configured.

The light guide 4 is removably coupled to the light source apparatus 3 at the one end and removably coupled to the insertion section 2 at the other end. The light guide 4 guides the light outputted from the light source apparatus 3 from the one end to the other end, supplying the light to the insertion section 2.

An eyepiece section 21 of the insertion section 2 is removably coupled to the camera head 5. The camera head 5 generates an imaging signal by capturing the observation image formed by the insertion section 2, converts the imaging signal (an electric signal) into an optical signal, and outputs it, under the control of the control apparatus 9. In addition, the camera head 5 includes a manipulation ring section 51 provided rotatably in a circumferential direction and plural input sections 52 that receive input of instruction signals for instructing various manipulations of the endoscope system 1.

The first transmission cable 6 is removably coupled to the control apparatus 9 via a first connector section 61 at one end and coupled to the camera head 5 via a second connector section 62 at the other end. The first transmission cable 6 enables transmitting the imaging signal outputted from the camera head 5 to the control apparatus 9 and transmitting a control signal outputted from the control apparatus 9, a synchronization signal, a clock signal, electricity, etc. to the camera head 5.

The display apparatus 7 displays, under the control of the control apparatus 9, a display image based on an image signal processed by the control apparatus 9 and various kinds of information regarding the endoscope system 1.

The second transmission cable 8 is removably coupled to the display apparatus 7 at one end and removably coupled to the control apparatus 9 at the other end. The second transmission cable 8 enables transmitting the display image based on the image signal processed by the control apparatus 9 to the display apparatus 7.

The control apparatus 9 includes a memory and a processor including hardware such as a CPU (Central Processing Unit), a GPU (Graphics Processing Unit), an ASIC (Application Specific Integrated Circuit), and an FPGA (Field Programmable Gate Array) and collectively controls, in accordance with a program recorded in the memory, operations of the light source apparatus 3, the camera head 5, and the display apparatus 7 through the first transmission cable 6, the second transmission cable 8, and the third transmission cable 10, respectively. The control apparatus 9 also outputs, to the light source apparatus 3, a signal for switching a wavelength band of light outputted from the light source apparatus 3 in accordance with a method of observation of the object. Here, the method of observation includes normal observation for which white light is outputted and special light observation for which light with a wavelength band different from a wavelength band of the white light is outputted. Embodiment 1 will be described by taking, as an example of the special light observation, IR observation, which is observation of fluorescence of indocyanine green injected or applied inside a body by outputting light having a wavelength band of infrared light.

The third transmission cable 10 is removably coupled to the light source apparatus 3 at one end and removably to the control apparatus 9 at the other end. The third transmission cable 10 enables transmitting the control signal from the control apparatus 9 to the light source apparatus 3.

[Detailed Configurations of Light Source Apparatus, Camera Head, and Control Apparatus]

Figure 2:
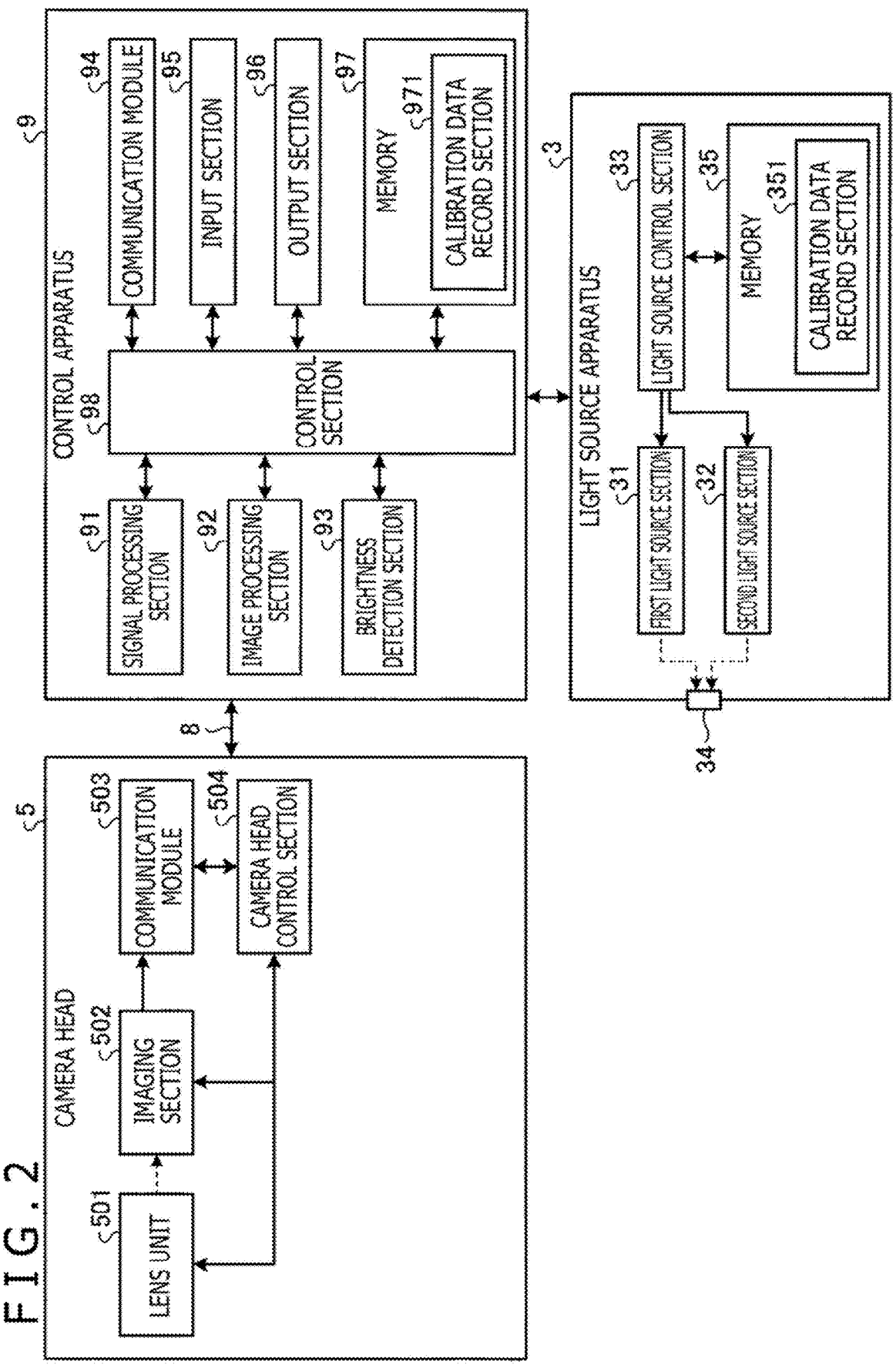
FIG. 2 is a block diagram illustrating functional configurations of a light source apparatus, a camera head, and a control apparatus of the endoscope system according to Embodiment 1.

Next, description will be made of functional configurations of the light source apparatus 3, the camera head 5, and the control apparatus 9. FIG. 2 is a block diagram illustrating the functional configurations of the light source apparatus 3, the camera head 5, and the control apparatus 9 of the endoscope system 1. It should be noted that, in FIG. 2, the insertion section 2, the light guide, the first transmission cable 6, the display apparatus 7, the second transmission cable 8, and the third transmission cable 10 are omitted for convenience of explanation.

[Configuration of Light Source Apparatus]

First, description will be made on the configuration of the light source apparatus 3.

The light source apparatus 3 includes a first light source section 31, a second light source section 32, and a light source control section 33.

The first light source section 31, which is capable of pulse emission, emits a first light for irradiating the object through the insertion section 2, thus supplying the light to the insertion section 2. Specifically, the first light source section 31 emits, under the control of the light source control section 33, light enabling white-color observation as the first light at a predetermined timing and for a predetermined emission time, thus supplying the light to the insertion section 2. The first light source section 31 includes a red semiconductor laser device capable of irradiation with a red (wavelength band: 600 to 700 nm) light, a blue semiconductor laser device capable of irradiation with a blue (wavelength band: 400 to 500 nm) light, and a green semiconductor laser device capable of irradiation with a green (wavelength band: 500 to 600 nm) light. It should be noted that the first light source section 31 includes the red, blue, and green semiconductor laser devices; however, this is not limiting and a white semiconductor laser device capable of irradiation with a white light may be used. In addition, the first light source section 31 is not necessarily a semiconductor laser device as long as pulse emission is possible and may be, for example, a light-emitting LED (Light Emitting Diode) or the like.

The second light source section 32, which is capable of pulse emission, emits a second light for irradiating the object through the insertion section 2. Specifically, the second light source section 32 emits, under the control of the light source control section 33, light that excites a fluorescent substance at a predetermined timing and for a predetermined emission time, thus supplying the light to the insertion section 2. More specifically, the second light source section 32 emits, under the control of the light source control section 33, an infrared light (wavelength band: 700 to 1000 nm) that excites a fluorescent substance, thus supplying the light to the insertion section 2. The second light source section 32 includes a semiconductor laser device capable of irradiation of light (700 to 1000 nm) that excites a fluorescent substance, a filter that only lets a predetermined wavelength band through, etc. It should be noted that the second light is described as an infrared light hereinbelow; however, it is not limiting and the second light may be, for example, light (wavelength band: around 405 nm) usable for PDD (Photo Dynamic Diagnosis) observation where fluorescence is observed with a photosensitive substance such as a hematoporphyrin derivative accumulated in a hematoporphyrin derivative in advance and light (wavelength band: 390 to 470 nm+wavelength band: 540 to 560 nm) usable for AFI (Auto Fluorescence Imaging) observation where autofluorescence from a fluorescent substance such as collagen is observed.

The light source control section 33 controls, under the control of the control apparatus 9, a pulse emission time of the first light emitted by the first light source section 31 and a pulse emission time of the second light emitted by the second light source section 32. Further, the light source control section 33 performs a control that maintains either one of the pulse emission time of the second light emitted by the second light source section 32 and a pulse emission intensity of the second light while performing a control that changes the other one of the pulse emission time and the pulse emission intensity of the second light. Further, the light source control section 33 controls each of the first light source section 31 and the second light source section 32, thereby performing a control that causes the first light and the second light to be alternately emitted on a frame-by-frame basis of the imaging signal generated by the camera head 5. In this case, the light source control section 33 maintains the pulse emission intensity of the second light during emission of the second light while controlling the pulse emission time. The light source control section 33 includes a memory and a processor including hardware such as a CPU, an ASIC, or an FPGA.

The connector section 34 is removably coupled to the one end of the light guide 4. The connector section 34 guides the light emitted by the first light source section 31 or the second light source section 32 to the light guide 4.

The memory 35 includes a volatile memory, a non-volatile memory, etc. The memory 35 records various kinds of data regarding the light source apparatus 3. The memory 35 includes a calibration data record section 351 that records calibration data including first calibration data in which a current value adjusted to allow the first light source section 31 to emit light at each of plural preset emission intensities and that is to be supplied to the first light source section 31 is associated and second calibration data in which a current value adjusted to allow the second light source section 32 to emit light at each of plural preset emission intensities and that is to be supplied to the second light source section 32 is associated. Further, the memory 35 stores color balance information regarding a color balance of each of the first light source section 31 and the second light source section 32. It should be noted that the memory 35 may further include a memory card attachable to the light source apparatus 3, or the like.

The light source apparatus 3 having such a configuration is set such that a brightness of a captured image corresponding to an imaging signal generated as a result of the camera head 5 (an imaging device) receiving light from the object irradiated with the first light with the pulse emission time and the pulse emission intensity of the first light emitted by the first light source section 31 maximized becomes higher than a brightness of a captured image corresponding to an imaging signal generated as a result of the camera head 5 (an imaging device) receiving light from the object irradiated with the second light with the pulse emission time and the pulse emission intensity of the second light emitted by the second light source section 32 maximized.

[Configuration of Camera Head]

Next, description will be made on the configuration of the camera head 5.

The camera head 5 includes a lens unit 501, an imaging section 502, a communication module 503, and a camera head control section 504.

The lens unit 501, which includes one or plural lenses, forms an image of a subject on a light-receiving surface of the imaging section 502. In addition, the lens unit 501 performs, under the control of the camera head control section 504, AF (Auto Focus) to change a focal position and optical zoom to change a focal distance by virtue of movement of the lens caused by a drive, which is not illustrated, along an optical axis direction. It should be noted that, in Embodiment 1, the lens unit 501 may be provided with a diaphragm mechanism and an optical filter mechanism that is removably insertable on an optical axis.

The imaging section 502 (an imaging device) generates, under the control of the camera head control section 504, an imaging signal (RAW data) by receiving the image of the subject formed by the insertion section 2 and the lens unit 501 and performing photoelectric conversion and outputs the imaging signal to the communication module 503. The imaging section 502 includes a CCD (Charge Coupled Apparatus), a CMOS (Complementary Metal Oxide Semiconductor), or the like.

The communication module 503 outputs various signals sent from the control apparatus 9 through the first transmission cable 6 to the sections in the camera head 5. In addition, the communication module 503 performs, through the first transmission cable 6, parallel/serial conversion processing or the like on the imaging signal generated by the imaging section 502, information regarding a current state of the camera head 5, etc. and outputs them to the control apparatus 9.

The camera head control section 504 controls the operations of the sections constituting the camera head 5 on the basis of the various signals inputted from the communication module 503. The camera head control section 504 includes a memory and a processor including hardware such as a CPU.

[Configuration of Control Apparatus]

Next, description will be made on the configuration of the control apparatus 9.

The control apparatus 9 includes a signal processing section 91, an image processing section 92, a brightness detection section 93, a communication module 94, an input section 95, an output section 96, and a memory 97.

The signal processing section 91 performs signal processing such as noise reduction processing and A/D conversion processing on the imaging signal inputted from the camera head 5 through the communication module 94 and outputs it to the image processing section 92, the brightness detection section 93, a control section 98, etc.

The image processing section 92 subjects the imaging signal inputted from the signal processing section 91 to predetermined image processing and outputs a display image for display, which is to be displayed on the display apparatus 7, to the display apparatus 7. Here, examples of the predetermined image processing include various kinds of known image processing such as interpolation processing, color correction processing, color enhancement processing, and contour enhancement processing. The image processing section 92 includes a memory and a processor including hardware such as a GPU, an FPGA, or a CPU. In addition, the image processing section 92 outputs a combined image that is a combination of a captured image corresponding to the imaging signal generated by the imaging section 502 during emission of the first light source section 31 and a captured image corresponding to the imaging signal generated by the imaging section 502 during emission of the second light source section 32 to the display apparatus 7.

The brightness detection section 93 detects a brightness of light applied from the light source apparatus 3 on the basis of a captured image corresponding to the imaging signal inputted from the signal processing section 91 and outputs a result of the detection to the control section 98.

The communication module 94 outputs various signals containing the imaging signal inputted from the camera head 5 and the signal inputted from the light source apparatus 3 to the control section 98 and the signal processing section 91. Further, the communication module 94 sends various signals inputted from the control section 98 to the camera head 5 and the light source apparatus 3. Specifically, the communication module 94 performs parallel/serial conversion processing or the like on the signals inputted from the control section 98 and outputs them to the camera head 5 and the light source apparatus 3. Further, the communication module 94 performs serial/parallel conversion processing or the like on the signals inputted from the camera head 5 and outputs them to the sections constituting the control apparatus 9.

The input section 95 includes a keyboard, a mouse, a touch panel, etc. The input section 95 receives input of various kinds of information based on manipulation of a user.

The output section 96 includes a speaker, a printer, a display, etc. The output section 96 outputs various kinds of information regarding the endoscope system 1.

The memory 97 includes a volatile memory, a non-volatile memory, a frame memory, etc. The memory 97 records a variety of programs that are to be executed by the endoscope system 1 and various kinds of data to be used during processing. The memory 97 records color balance information regarding the color balance of each of the first light source section 31 and the second light source section 32. In addition, the memory 97 includes a calibration data record section 971 that acquires, responsive to the light source apparatus 3 being coupled, calibration from the calibration data record section 351 of the memory 35 of the light source apparatus 3 and records the acquired calibration data. It should be noted that calibration data recorded in an external server or the like may be recorded in the calibration data record section 971 via the communication module 94. In addition, the memory 97 may further include a memory card attachable to the control apparatus 9, or the like.

The control section 98 collectively controls the sections constituting the endoscope system 1. The control section 98 includes a memory and hardware such as a CPU. The control section 98 outputs, on the basis of an observation method switching signal inputted from the input section 95, a signal for switching the wavelength band of light to be outputted from the light source apparatus 3 and a light-modulation signal for modulating the brightness of the captured image to the light source apparatus 3.

[Typical Time-Division Exposure]

Figure 3:
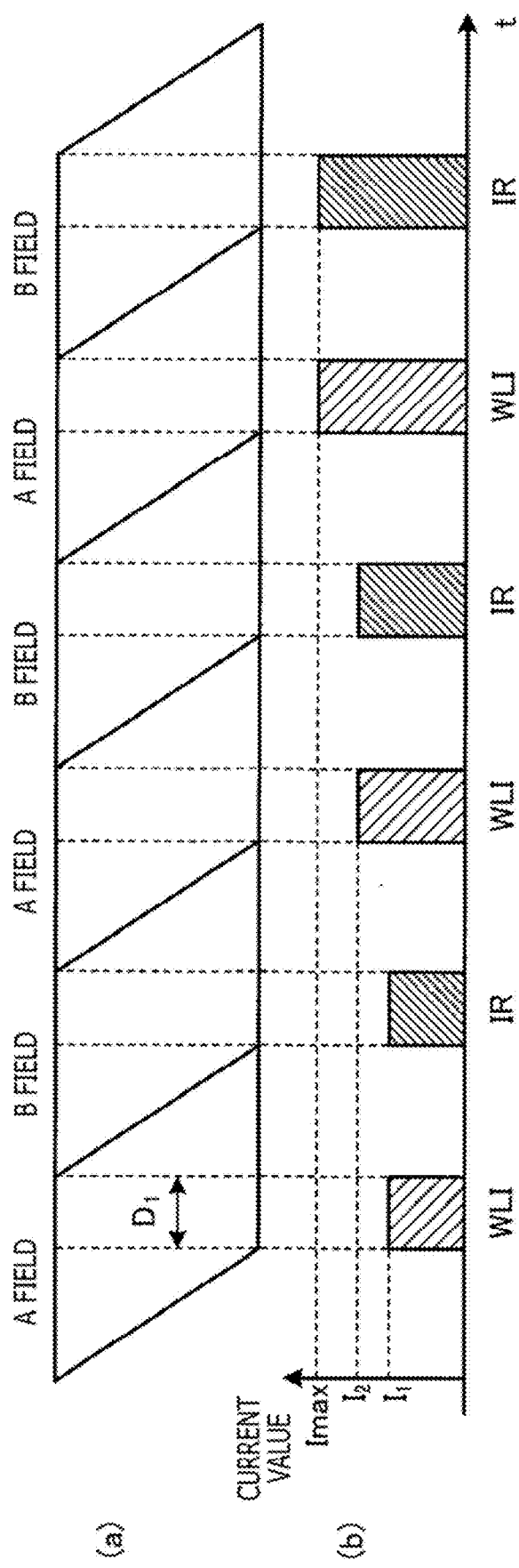
FIG. 3 is a timing chart schematically illustrating an operation for enhancing brightness by typical time-division exposure to be performed by the endoscope system according to Embodiment 1.
Figure 4:
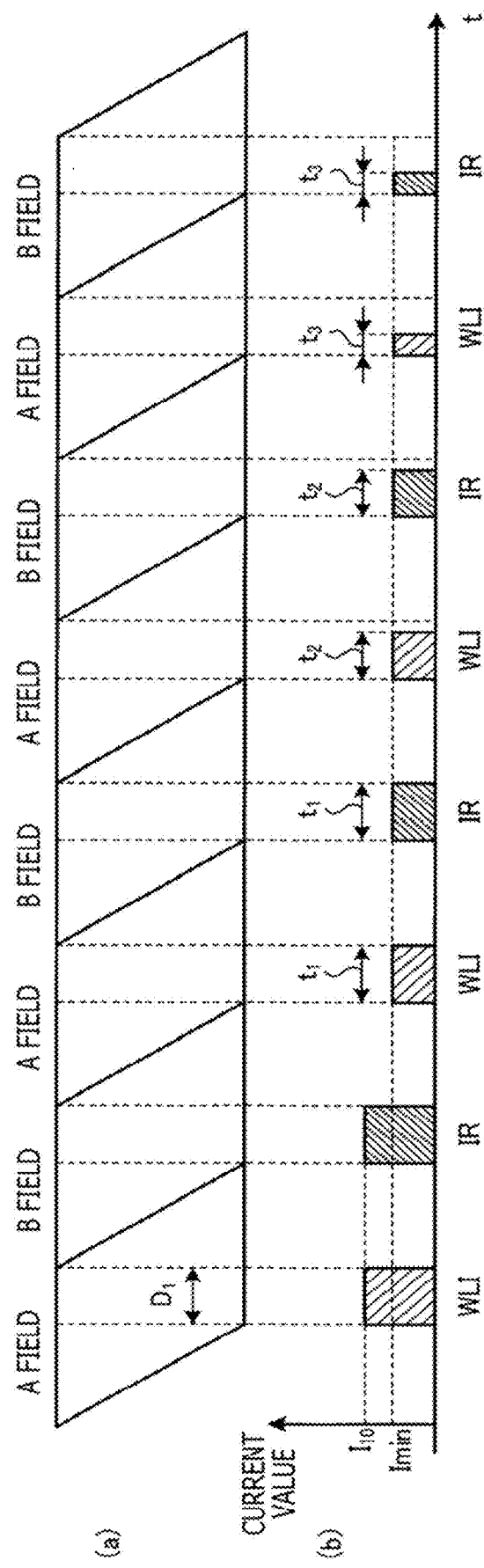
FIG. 4 is a timing chart schematically illustrating an operation for lowering brightness by the typical time-division exposure to be performed by the endoscope system according to Embodiment 1.

Next, description will be made on typical time-division exposure to be performed by the endoscope system 1. FIG. 3 is a timing chart schematically illustrating an operation for enhancing brightness by the typical time-division exposure to be performed by the endoscope system 1. FIG. 4 is a timing chart schematically illustrating an operation for lowering brightness by the typical time-division exposure to be performed by the endoscope system 1. In addition, (a) in FIG. 3 and (a) in FIG. 4 illustrate frame-by-frame fields of imaging signals continuously generated by the imaging section 502. Further, in (b) in FIG. 3 and (b) in FIG. 4, an abscissa axis represents time and an ordinate axis represents a current value. In addition, referring to FIG. 3 and FIG. 4, description will be made on a case where the endoscope system 1 causes the light source apparatus 3 to alternately emit a white light WLI, which is the first light, and an infrared light IR, which is the second light, and perform irradiation through the insertion section 2. It should be noted that, in FIG. 3 and FIG. 4, magnitudes of the white light WLI and the infrared light IR at a maximum current value $I_{max}$ are expressed substantially the same in height for simplification of explanation; however, it should be understood that there is actually a difference in magnitude between the white light WLI and the infrared light IR at the maximum current value $I_{max}$.

[Case of Enhancing Brightness of Captured Image by Typical Time-Division Exposure]

First, description will be made on a case of enhancing a brightness of a captured image by the typical time-division exposure to be performed by the endoscope system 1.

As illustrated in FIG. 3, to prevent the occurrence of a stripe pattern attributed to unevenness of exposure on a display image, the light source control section 33 causes the first light source section 31 and the second light source section 32 to emit light only for a full-line exposure period $D_1$ for the imaging section 502 in each field. Further, the light source control section 33 repeats, as one set, an operation for causing the first light source section 31 and the second light source section 32 to alternately emit. Specifically, the light source control section 33 causes the first light source section 31 to emit the white light WLI in an A field and causes the second light source section 32 to emit the infrared light IR in a B field.

Subsequently, the light source control section 33 performs, on the basis of an instruction signal indicating a brightness of a captured image corresponding to an imaging signal inputted from the control apparatus 9, a control that increases an amount of current of each of the first light source section 31 and the second light source section 32 on a set-by-set basis until the maximum current value $I_{max}$ is reached (current value $I_1 \rightarrow$ current value $I_2 \rightarrow$ maximum current value $I_{max}$). This enhances intensities of the white light WLI and the infrared light IR on a field-by-field basis, thus increasing the brightness of the captured image corresponding to the imaging signal.

[Case of Lowering Brightness by Typical Time-Division Exposure]

Next, description will be made on a case of lowering brightness by the typical time-division exposure to be performed by the endoscope system 1.

First, the light source control section 33 performs, on the basis of an instruction signal indicating a brightness of a captured image corresponding to an imaging signal inputted from the control apparatus 9, current control that reduces the current value of each of the first light source section 31 and the second light source section 32 on a set-by-set basis until a minimum current value $I_{min}$ is reached (current value $I_{10} \rightarrow$ minimum current value $I_{min}$) as illustrated in FIG. 4. This reduces the intensities of the white light WLI and the infrared light IR on a field-by-field basis. As a result, the brightness of the captured image corresponding to the imaging signal is lowered.

In addition, in a case where the light source control section 33 lowers the current values of the first light source section 31 and the second light source section 32 below the respective minimum current values $I_{min}$, the first light source section 31 and the second light source section 32 each stop emitting light. Accordingly, after the respective minimum current values $I_{min}$ of the first light source section 31 and the second light source section 32 are reached, the light source control section 33 performs a control that reduces respective pulse emission times of the first light source section 31 and the second light source section 32 on a set-by-set basis (emission time $t_1 \rightarrow$ emission time $t_2 \rightarrow$ emission time $t_3$). This reduces the intensities of the white light WLI and the infrared light IR on a field-by-field basis. As a result, the brightness of the captured image corresponding to the imaging signal is lowered.

As is understood from the above, in the typical time-division exposure, to lower a brightness of a captured image, the light source control section 33 first performs the current control that reduces the current values to the respective minimum current values of the first light source section 31 and the second light source section 32. After that, the light source control section 33 performs the control that makes the respective pulse emission times of the first light source section 31 and the second light source section 32 shorter. Therefore, in the typical time-division exposure, a change in current value and pulse emission time leads to disruption of a color balance of the captured image due to a difference in spectroscopic characteristics and functional characteristics between the first light source section 31 and the second light source section 32. Accordingly, the endoscope system 1 that performs the typical time-division exposure necessitates, during a product inspection before shipping, measuring the respective spectroscopic characteristics and functional characteristics of the first light source section 31 and the second light source section 32 and storing parameters of the respective current values and pulse emission times adjusted in terms of the color balance of the captured image in a memory or the like. A work for an adjustment work has thus typically disadvantageously been complicated.

[Time-Division Exposure of Present Disclosure]

Figure 5:
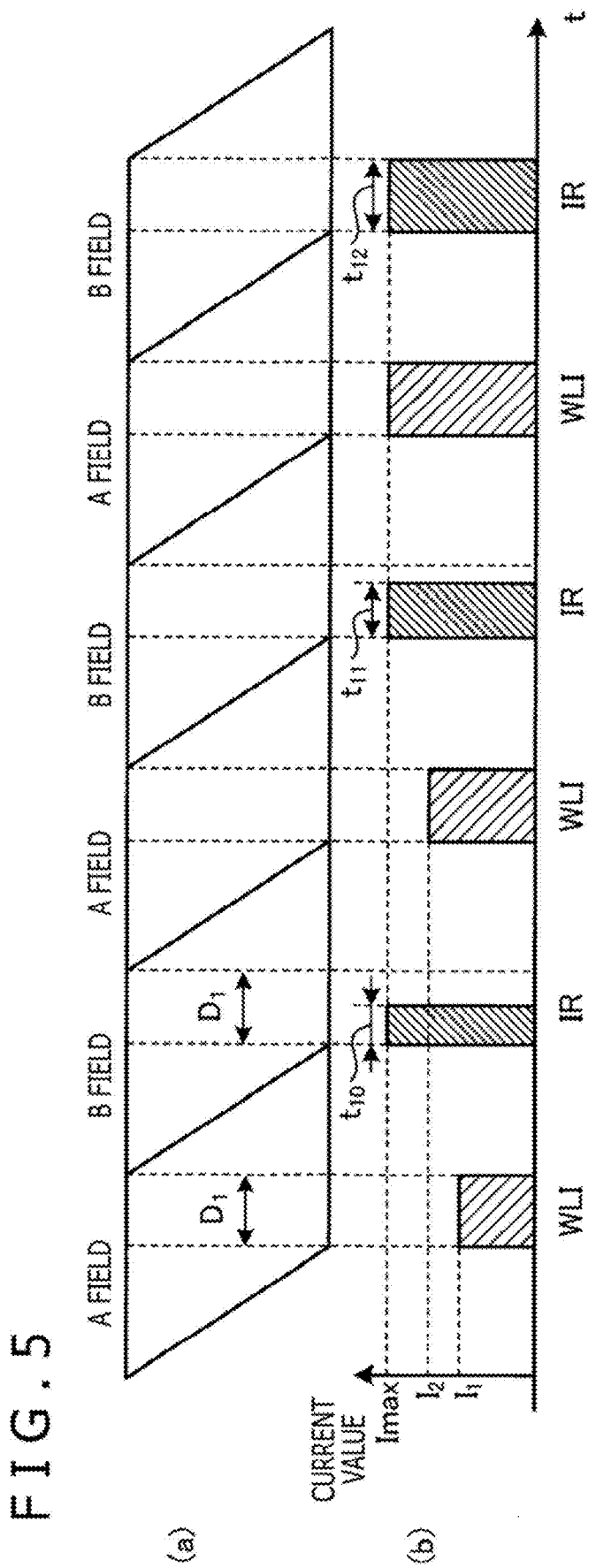
FIG. 5 is a timing chart schematically illustrating an operation for enhancing brightness by time-division exposure to be performed by the endoscope system according to Embodiment 1.
Figure 6:
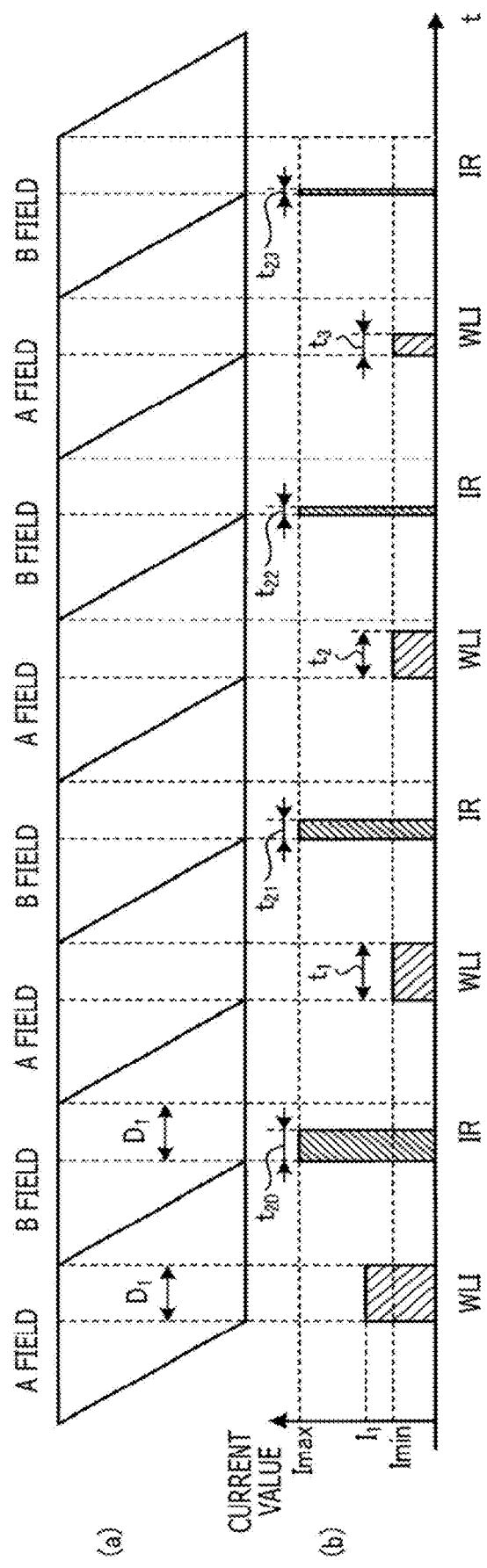
FIG. 6 is a timing chart schematically illustrating an operation for lowering brightness by the time-division exposure to be performed by the endoscope system according to Embodiment 1.

Next, description will be made on time-division exposure of the present disclosure to be performed by the endoscope system 1. FIG. 5 is a timing chart schematically illustrating an operation for enhancing brightness by time-division exposure to be performed by the endoscope system 1. FIG. 6 is a timing chart schematically illustrating an operation for lowering brightness by the time-division exposure to be performed by the endoscope system 1. In addition, (a) in FIG. 5 and (a) in FIG. 6 illustrate frame-by-frame fields of imaging signals continuously generated by the imaging section 502. Further, in (b) in FIG. 5 and (b) in FIG. 5, an abscissa axis represents time and an ordinate axis represents a current value. It should be noted that, in FIG. 5 and FIG. 6, the magnitudes of the white light WLI and the infrared light IR at the maximum current value $I_{max}$ are expressed substantially the same in height for simplification of explanation; however, it should be understood that there is actually a difference in magnitude between the white light WLI and the infrared light IR at the maximum current value $I_{max}$.

[Case of Enhancing Brightness of Captured Image by Time-Division Exposure]

First, description will be made on a case of enhancing a brightness of a captured image by the time-division exposure to be performed by the endoscope system 1.

As illustrated in FIG. 5, the light source control section 33 performs a control that prolongs the pulse emission time of the second light source section 32 on a field-by-field basis by increasing a ratio of PWM control with the current value of the second light source section 32 fixed at the maximum current value $I_{max}$ (time $t_{10} \rightarrow$ time $t_{11} \rightarrow$ time $t_{12}$). An image captured with the infrared light IR, which is equivalent to an image captured by monochrome observation, does not need to be subjected to a fine light source control. Accordingly, the light source control section 33 performs a control that prolongs the pulse emission time of the infrared light IR emitted by the second light source section 32.

In contrast, the light source control section 33 performs a control that increases the current value of the first light source section 31 on a field-by-field basis until the maximum current value $I_{max}$ is reached (current value $I_1 \rightarrow$ current value $I_2 \rightarrow$ maximum current value $I_{max}$) as illustrated in FIG. 5. In this case, a brightness of a captured image corresponding to an imaging signal generated as a result of the camera head 5 (an imaging device) receiving light from the object with the pulse emission time and the pulse emission intensity of the first light emitted by the first light source section 31 maximized becomes higher than a brightness of a captured image corresponding to an imaging signal generated as a result of the camera head 5 (an imaging device) receiving light from the object with the pulse emission time and the pulse emission intensity of the second light emitted by the second light source section 32 maximized. In addition, an image captured with the white light WLI needs to be prevented from color-balance disruption. Accordingly, the light source control section 33 performs the pulse emission intensity of the white light WLI emitted by the first light source section 31 by controlling the current value, thereby performing an accurate light modulation control.

[Case of Lowering Brightness of Captured Image by Time-Division Exposure]

Next, description will be made on a case of lowering a brightness of a captured image by the time-division exposure to be performed by the endoscope system 1.

As illustrated in FIG. 6, the light source control section 33 performs, on the basis of an instruction signal indicating a brightness of a captured image corresponding to an imaging signal inputted from the control apparatus 9, a control that reduces the current value of the first light source section 31 on a field-A-by-field-A basis until the minimum current value $I_{min}$ is reached (current value $I_{10} \rightarrow$ minimum current value $I_{min}$). The light source control section 33 then performs a control that reduces the pulse emission time of the first light source section 31 on an A-field-by-A-field basis (emission time $t_1 \rightarrow$ emission time $t_2 \rightarrow$ emission time $t_3$).

In contrast, the light source control section 33 performs a control that shortens the pulse emission time of the second light source section 32 on a B-field-by-B-field basis with the current value of the second light source section 32 fixed at the maximum current value $I_{max}$ (time $t_{20} \rightarrow$ time $t_{21} \rightarrow$ time $t_{22} \rightarrow$ time $t_{23}$).

According to above-described Embodiment 1, the light source control section 33 controls each of the pulse emission time and the pulse emission intensity of the first light emitted by the first light source section 31 and performs the control that changes the pulse emission time of the second light with the pulse emission intensity of the second light emitted by the second light source section 32 fixed, which makes it possible to subject the second light source section 32 to light modulation only by PWM light modulation without the necessity of performing a complicated work.

In addition, according to Embodiment 1, a brightness of a captured image corresponding to an imaging signal generated as a result of the imaging section 502 receiving light from the object with the pulse emission time and the pulse emission intensity of the first light emitted by the first light source section 31 maximized becomes higher than a brightness of a captured image corresponding to an imaging signal generated as a result of the imaging section 502 receiving light from the object with the pulse emission time and the pulse emission intensity of the second light emitted by the second light source section 32 maximized. Accordingly, the infrared light IR emitted by the second light source section 32 is equivalent to monochrome observation, so that a fine current control can be omitted.

Further, according to Embodiment 1, the first light source section generates the white light WLI as the first light and the second light source section 32 generates the infrared light IR, which excites a fluorescent substance, as the second light. This makes it possible to perform normal observation and special observation.

In addition, according to Embodiment 1, the light source control section 33 performs the control that causes the first light source section 31 and the second light source section 32 to alternately emit light and performs the control that changes the pulse emission time with the pulse emission intensity of the second light during emission from the second light source section 32 fixed. This makes it possible to generate a combined image that is a combination of a white image with a fluorescence image.

It should be noted that, in Embodiment 1, the light source control section 33 performs the control that changes the pulse emission time of the second light with the pulse emission intensity of the second light emitted by the second light source section 32 fixed; however, the pulse emission intensity of the second light may be changed with the pulse emission time of the second light fixed.

In addition, in Embodiment 1, the light source apparatus 3 causes the white light WLI and the infrared light IR to be alternately emitted; however, it is not limiting and, for example, a light source section capable of emitting a third light may be provided and the first light, the second light, and the third light may be sequentially emitted in this order as one set. In this case, it is sufficient that the third light includes a narrow band light for NBI (Narrow Band Imaging), a light by PDD observation, and light by AFI observation.

Embodiment 2

Next, Embodiment 2 will be described. In above-described Embodiment 1, description is made on the case of application to the rigid endoscope system including a rigid scope, whereas description will be made on a case of application to a flexible endoscope system including a flexible endoscope in Embodiment 2. It should be noted that the same reference signs are used to refer to the same components as those of the endoscope system 1 according to above-described Embodiment 1, and a detailed description thereof will be omitted.

[Schematic Configuration of Endoscope System]

Figure 7:
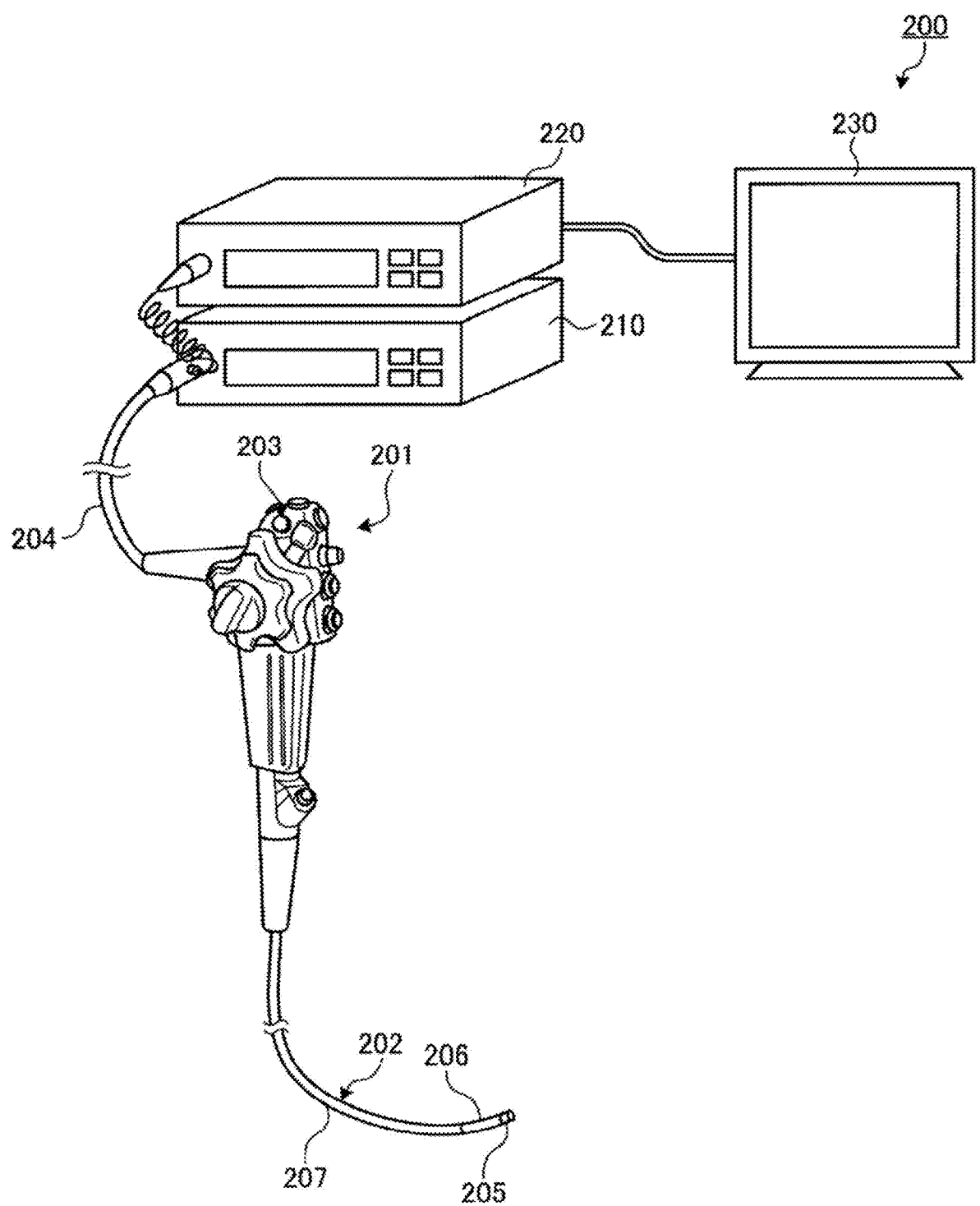
FIG. 7 illustrates a schematic configuration of an endoscope system according to Embodiment 2.

FIG. 7 illustrates a schematic configuration of an endoscope system according to Embodiment 2. An endoscope system 200 illustrated in FIG. 7 includes an endoscope 201 that captures an internal body image of a part to observe by inserting an insertion section 202 into a body of an object and generates an imaging signal, a light source apparatus 210 that supplies the first light and the second light to the endoscope 201, a control apparatus 220 that subjects the imaging signal acquired by the endoscope 201 to predetermined image processing and collectively controls an operation of the entire endoscope system 200, and a display apparatus 230 that displays the internal body image subjected to the image processing by the control apparatus 220.

The light source apparatus 210 includes the above-described first light source section 31, second light source section 32, and light source control section 33. The light source apparatus 210 supplies, under the control of the control apparatus 220, the first light and the second light to the endoscope 201.

The control apparatus 220 includes at least the above-described signal processing section 91, image processing section 92, brightness detection section 93, memory 97, and control section 98.

According to above-described Embodiment 2, even the flexible endoscope system 200 can achieve effects similar to those of above-described Embodiment 1.

Embodiment 3

Next, Embodiment 3 will be described. In Embodiment 3, description will be made on a case of application to a surgical microscope system instead of the endoscope system in above-described Embodiments 1 and 2. It should be noted that the same reference signs are used to refer to the same components as those of the endoscope system 1 according to above-described Embodiment 1, and a detailed description thereof will be omitted.

[Configuration of Surgical Microscope System]

Figure 8:
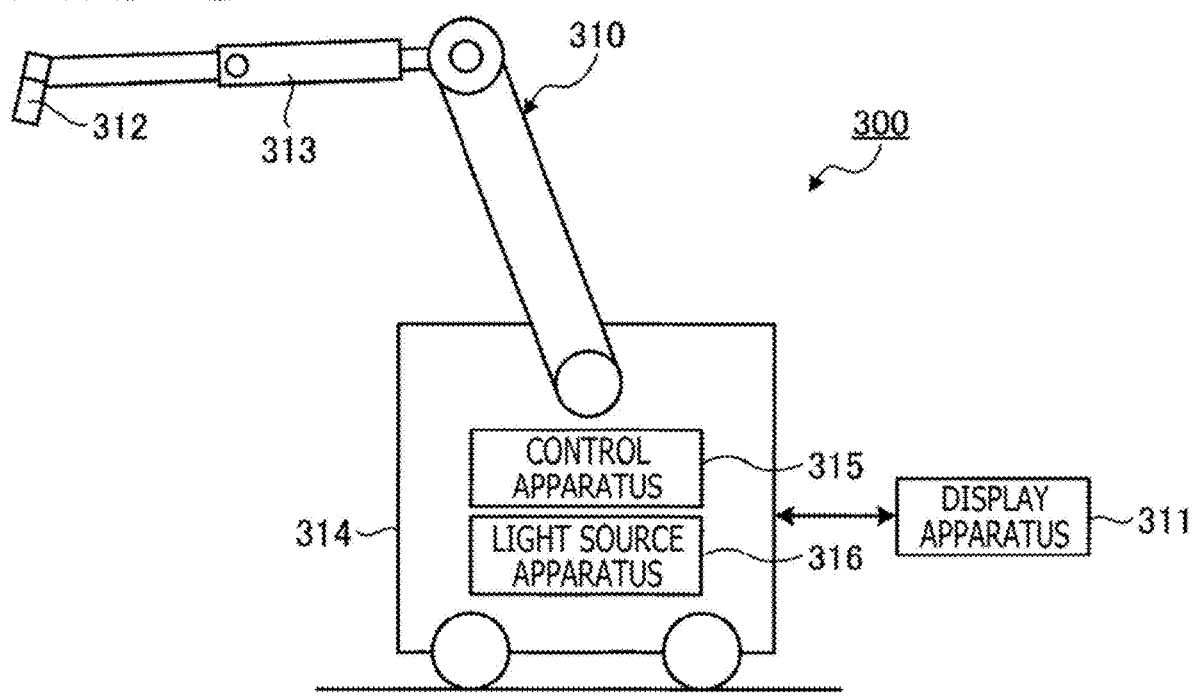
FIG. 8 illustrates a schematic configuration of a surgical microscope system according to Embodiment 3.

FIG. 8 illustrates a schematic configuration of a surgical microscope system according to Embodiment 3. A surgical microscope system 300 illustrated in FIG. 8 includes a microscope apparatus 310 in the form of a medical imaging apparatus that performs imaging to acquire an image for observing a subject and a display apparatus 311 that displays the image captured by the microscope apparatus 310. It should be noted that the display apparatus 311 and the microscope apparatus 310 can be integrated with each other.

The microscope apparatus 310 includes a microscope section 312 that captures an image of a micro part of the subject in closeup, a support section 313 including an arm coupled to a base end portion of the microscope section 312 and by which the microscope section 312 is pivotally supported, and a base section 314 by which a base end portion of the support section 313 is pivotally held and that is movable on a floor surface. The base section 314 includes a control apparatus 315 that controls an operation of the surgical microscope system 300 and a light source apparatus 316 that generates an illumination light to be applied to the subject from the microscope apparatus 310. It should be noted that the control apparatus 315 includes at least the above-described signal processing section 91, image processing section 92, brightness detection section 93, memory 97, and control section 98. In addition, the light source apparatus 316 includes the first light source section 31, the second light source section 32, and the light source control section 33. In addition, the base section 314 may be fixed to a ceiling, a wall surface, or the like to support the support section 313 instead of being provided movably on the floor surface.

The microscope section 312, which is, for example, in a columnar shape, includes the above-escribed lens unit 501 and imaging section 502 therein. A side surface of the microscope section 312 is provided with a switch for receiving input of instructions regarding an operation of the microscope apparatus 310. An opening surface of a lower end portion of the microscope section 312 is provided with a cover glass for protecting inside (not illustrated).

The surgical microscope system 300 having such a configuration causes the microscope section 312 to move, performs zooming, and switches the illumination light in response to a user such as an operator operating various switches while grasping the microscope section 312. Incidentally, it is preferable that the microscope section 312 be in a shape elongated in an observation direction such that a user can easily hold the microscope section 312 and change a view direction. Accordingly, the microscope section 312 may be in a shape other than a columnar shape, for example, in a shape of a polygonal prism.

According to above-described Embodiment 3, the surgical microscope system 300 can also achieve effects similar to those of above-described Embodiment 1.

Embodiment 4

Next, Embodiment 4 will be described. In above-described Embodiment 1, the calibration data including the first calibration of the first light source section 31 and the second calibration of the second light source section 32 is recorded in the light source apparatus 3 in advance, whereas in Embodiment 4, calibration processing is performed by using an adjustment apparatus during inspection of the light source apparatus 3 before shipping and calibration data generated by the calibration processing is recorded in the calibration data record section 351. It should be noted that the same reference signs are used to refer to the same components as those of the endoscope system 1 according to above-described Embodiment 1, and a detailed description thereof will be omitted.

Figure 9:
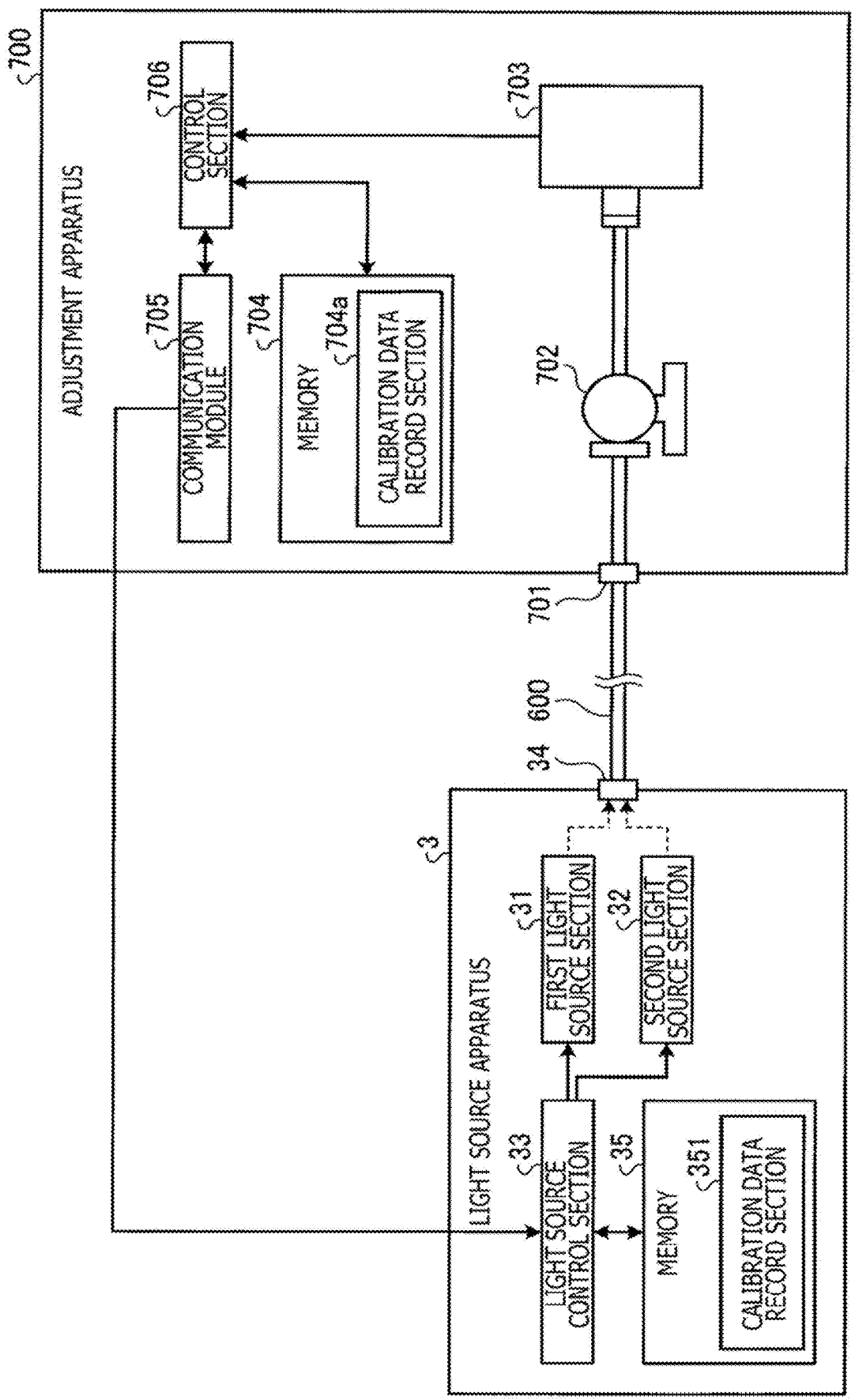
FIG. 9 is a block diagram illustrating functional configurations of a light source apparatus and an adjustment apparatus according to Embodiment 4.

FIG. 9 is a block diagram illustrating functional configurations of the light source apparatus 3 and an adjustment apparatus 700. The adjustment apparatus 700 illustrated in FIG. 9 generates calibration data including first calibration of the first light source section 31 and second calibration of the second light source section 32 of the light source apparatus 3 and records the generated calibration data in the calibration data record section 351. The light source apparatus 3 and the adjustment apparatus 700 are optically coupled to each other through a light guide 600.

[Configuration of Adjustment Apparatus]

The adjustment apparatus 700 illustrated in FIG. 9 includes a connector section 701, an integrating sphere 702, a spectrometer 703, a memory 704, a communication module 705, and a control section 706.

The connector section 701, to which the light guide 600 is removably coupled, guides light emitted by the first light source section 31 or the second light source section 32 of the light source apparatus 3 to the integrating sphere 702.

The integrating sphere 702 causes the light entering through the connector section 701 to be repeatedly diffused and reflected on an inner wall and causes the diffused and reflected light to enter the spectrometer 703. The integrating sphere 702 is implemented by a hollow sphere with an inner wall front surface coated with powder having a high reflectance (diffusion and reflection rate).

The spectrometer 703 measures a brightness per wavelength band of the light entering from the integrating sphere 702 and outputs a result of the measurement to the control section 706. The spectrometer 703 is implemented by a spectroscope that splits the light entering from the integrating sphere 702 and a detector such as an image sensor that detects light passing through the spectroscope. It should be noted that the spectrometer 703 functions as a measurement section in Embodiment 4.

The memory 704 includes a volatile memory, a nonvolatile memory, etc. The various programs to be performed by the adjustment apparatus 700 and data being processed are recorded in the memory 704. Further, the memory 704 includes a calibration data record section 704a that records calibration data of each of plural light source apparatuses 3 adjusted by the adjustment apparatus 700 before shipping.

The communication module 705 outputs various signals, which contain the calibration data inputted from the control section 706, to the calibration data record section 351 via the light source control section 33 of the light source apparatus 3. The communication module 705 performs parallel/serial conversion processing or the like on the calibration data inputted from the control section 706 and outputs the calibration data to the calibration data record section 351 via the light source control section 33 of the light source apparatus 3.

The control section 706 collectively controls the sections constituting the adjustment apparatus 700. The control section 706 includes a memory and hardware such as a CPU. The control section 706 controls the light source control section 33, thereby causing the first light source section 31 to emit light (emit a pulse) at a predetermined current value and acquiring an emission intensity (a pulse emission intensity) measured by the spectrometer 703 during emission from the first light-emitting section 31. The control section 706 then controls the light source control section 33 such that the first light source section 31 achieves each of plural preset emission intensities, thereby adjusting a current value to be supplied to the first light source section 31. After that, the control section 706 generates the first calibration data, in which the plural preset emission intensities of the first light source section 31 are associated with plural respective current values. In addition, the control section 706 controls the light source control section 33, thereby causing the second light source section 32 to emit light at a predetermined current value (maximum current value) and acquiring an emission intensity measured by the spectrometer 703 during emission from the second light-emitting section 32. The control section 706 then controls the light source control section 33 such that the second light source section 32 achieves each of plural preset emission intensities, thereby adjusting a current value to be supplied to the second light source section 32. After that, the control section 706 generates the second calibration data, in which the plural preset emission intensities of the second light source section 32 are associated with plural respective current values. At the end, the control section 706 causes the calibration data including the first calibration data and the second calibration data to be recorded in the calibration data record section 704a and recorded, via the light source control section 33 of the light source apparatus 3, in the calibration data record section 351.

[Adjustment Method by Adjustment Apparatus]

Figure 10:
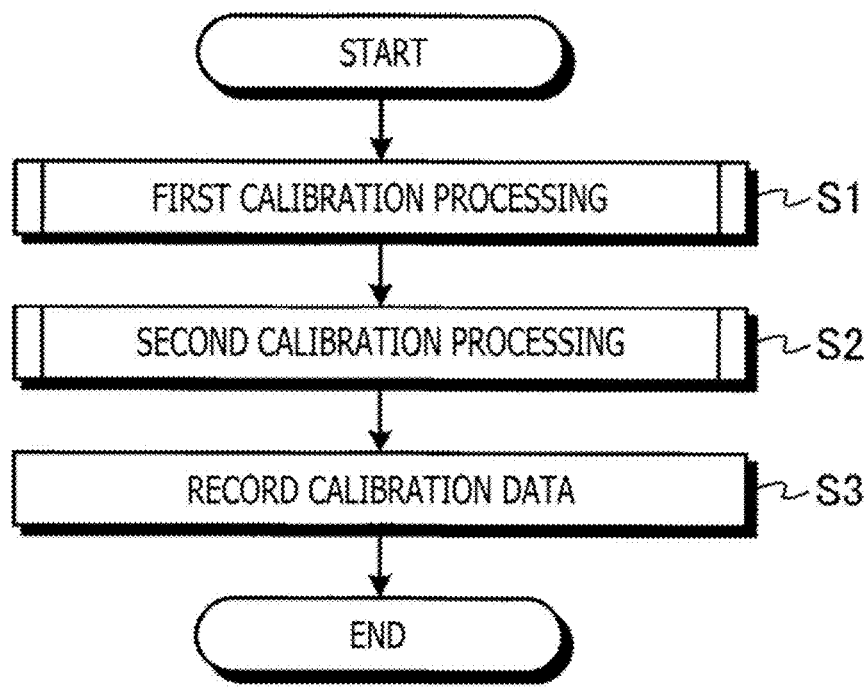
FIG. 10 is a flowchart illustrating an outline of a process of an adjustment method to be performed by an adjustment apparatus 700 according to Embodiment 4.

Next, description will be made on an adjustment method by the adjustment apparatus 700 for the emission intensity and the current value of each of the first light-emitting section 31 and the second light-emitting section 32 of the light source apparatus 3. FIG. 10 is a flowchart illustrating an outline of a process of the adjustment method to be performed by the adjustment apparatus 700.

As illustrated in FIG. 10, the control section 706 performs first calibration processing for associating plural emission intensities of light to be emitted by the first light source section 31 with plural current values (Step S1). After Step S1, the adjustment apparatus 700 advances to later-described Step S2.

[First Calibration Processing]

Figure 11:
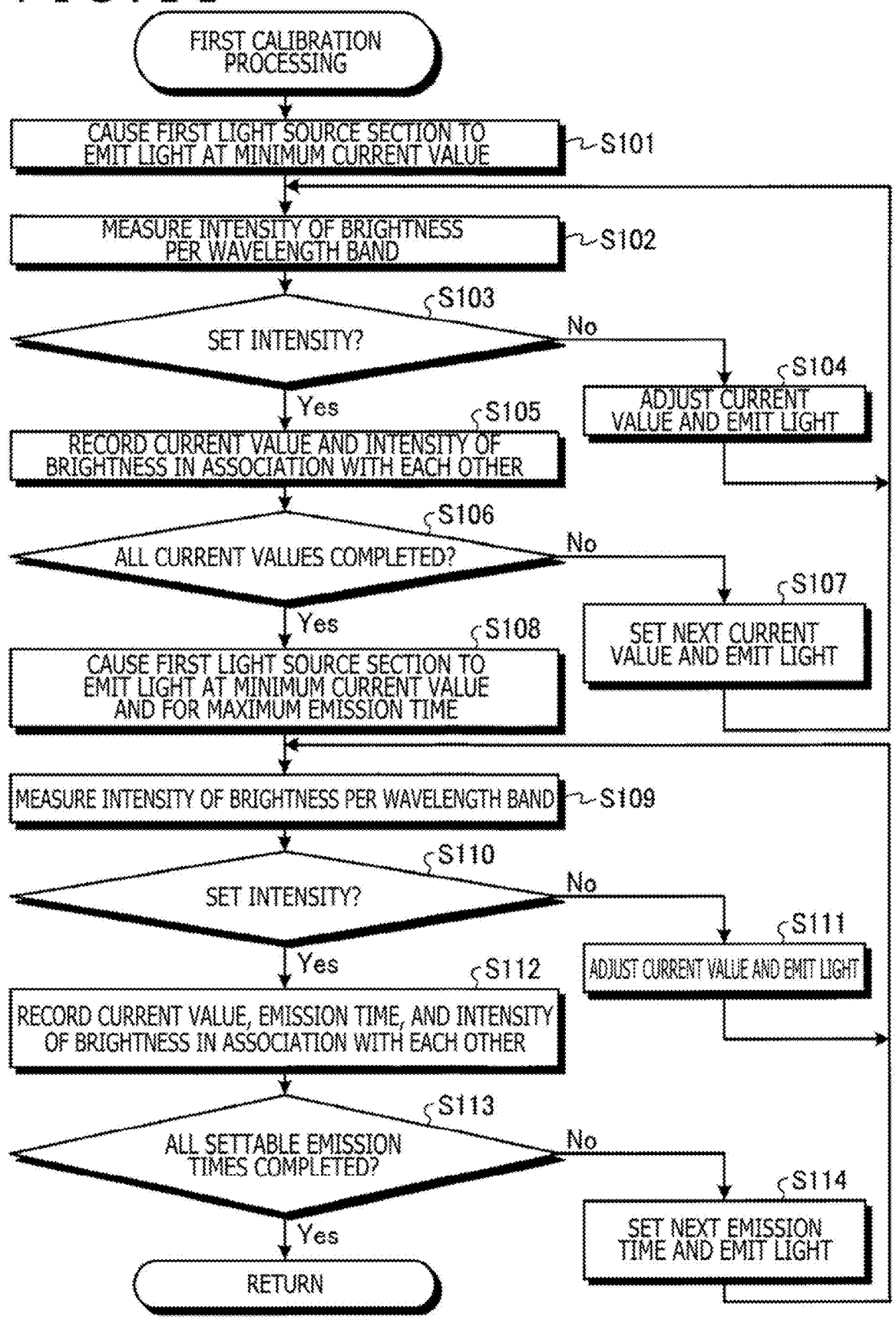
FIG. 11 is a flowchart illustrating an outline of first calibration processing in FIG. 10.

FIG. 11 is a flowchart illustrating an outline of the first calibration processing in Step S1 in FIG. 10.

As illustrated in FIG. 11, the control section 706 first causes the first light source section 31 to emit light at the minimum current value by controlling the light source control section 33 (Step S101) and causes the spectrometer 703 to measure an intensity of brightness per wavelength band of the light entering through the integrating sphere 702 (Step S102).

Subsequently, the control section 706 determines whether or not the intensity of brightness per wavelength band measured by the spectrometer 703 is the set intensity (Step S103). In a case where the control section 706 determines that the intensity of brightness per wavelength band measured by the spectrometer 703 is the set intensity (Step S103: Yes), the adjustment apparatus 700 advances to later-described Step S105. In contrast, in a case where the control section 706 determines that the intensity of brightness per wavelength band measured by the spectrometer 703 is not the set intensity (Step S103: No), the adjustment apparatus 700 advances to later-described Step S104.

In Step S104, the control section 706 adjusts, on the basis of a difference between the intensity of brightness per wavelength band measured by the spectrometer 703 and the set intensity, the current value to be supplied to the first light source section 31 by the light source control section 33 and causes the first light source section 31 to emit light. After Step S104, the adjustment apparatus 700 returns to above-described Step S102.

In Step S105, the control section 706 causes the calibration data record section 704a to record the current value to be supplied to the first light source section 31 by the light source control section 33 and the intensity of brightness per wavelength band measured by the spectrometer 703 in association with each other.

Subsequently, the control section 706 determines whether or not all the preset intensities have been completed (Step S106). In a case where the control section 706 determines that all the preset intensities have been completed (Step S106: Yes), the adjustment apparatus 700 advances to later-described Step S108. In contrast, in a case where the control section 706 determines that all the preset intensities have not been completed (Step S106: No), the adjustment apparatus 700 advances to later-described Step S107.

In Step S107, the control section 706 sets the current value to be supplied to the first light source section 31 by the light source control section 33 at next one of the preset current values and the first light source section 31 is caused to emit light. After Step S107, the adjustment apparatus 700 returns to above-described Step S102.

In Step S108, the control section 706 causes the first light source section 31 to emit light at the minimum current value and for the predetermined emission time by controlling the light source control section 33.

Subsequently, the control section 706 causes the spectrometer 703 to measure an intensity of brightness per wavelength band of the light entering through the integrating sphere 702 (Step S109).

After that, the control section 706 determines whether or not the intensity of brightness per wavelength band measured by the spectrometer 703 is the set intensity (Step S110). In a case where the control section 706 determines that the intensity of brightness per wavelength band measured by the spectrometer 703 is the set intensity (Step S110: Yes), the adjustment apparatus 700 advances to later-described Step S112. In contrast, in a case where the control section 706 determines that the intensity of brightness per wavelength band measured by the spectrometer 703 is not the set intensity (Step S110: No), the adjustment apparatus 700 advances to later-described Step S111.

In Step S111, the control section 706 adjusts the emission time for which the light source control section 33 causes the first light source section 31 to emit light on the basis of a difference between the intensity of brightness per wavelength band measured by the spectrometer 703 and the set intensity and causes the first light source section 31 to emit light. After Step S111, the adjustment apparatus 700 returns to above-described Step S109.

In Step S112, the control section 706 generates the first calibration data, in which the current value to be supplied to the first light source section 31 by the light source control section 33, the emission time, and the intensity of brightness per wavelength band measured by the spectrometer 703 are associated with each other, and causes the calibration data record section 704a to record the first calibration data.

Subsequently, the control section 706 determines whether or not all the emission times settable for the first light source section 31 by the light source control section 33 have been completed (Step S113). In a case where the control section 706 determines that all the emission times settable for the first light source section 31 by the light source control section 33 have been completed (Step S113: Yes), the adjustment apparatus 700 returns to the above-described main routine in FIG. 10, advancing to Step S2. In contrast, in a case where the control section 706 determines that all the emission times settable for the first light source section 31 by the light source control section 33 have not been completed (Step S113: No), the adjustment apparatus 700 advances to later-described Step S114.

In Step S114, the control section 706 sets the emission time for which the light source control section 33 causes the first light source section 31 to emit light at next one of the emission times and the first light source section 31 is caused to emit light. After Step S114, the adjustment apparatus 700 returns to above-described Step S109.

Referring back to FIG. 10, description will be made on Step S2 and later.

In Step S2, the control section 706 performs the first calibration processing for associating the plural emission intensities at which the first light source section 31 is to emit light with the plural current values (Step S1). After Step S1, the adjustment apparatus 700 advances to later-described Step S2.

[Second Calibration Processing]

Figure 12:
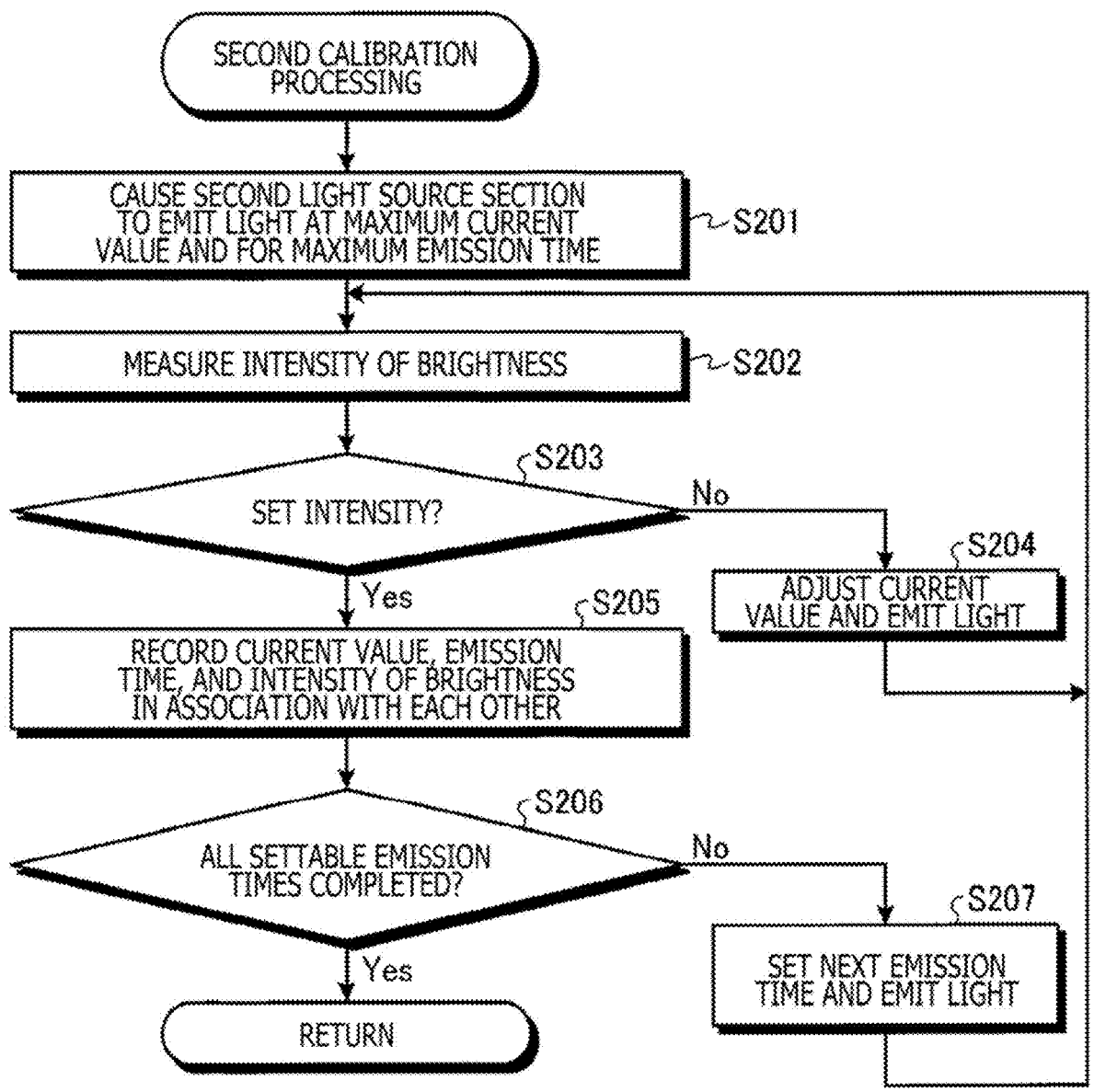
FIG. 12 is a flowchart illustrating an outline of second calibration processing in FIG. 10.

FIG. 12 is a flowchart illustrating an outline of the second calibration processing in Step S2 in FIG. 10.

As illustrated in FIG. 12, the control section 706, the control section 706 first causes the second light source section 32 to again emit light at the current value and for the maximum emission time by controlling the light source control section 33 (Step S201) and causes the spectrometer 703 to measure an intensity of brightness of wavelength band of the light entering through the integrating sphere 702 (Step S202).

Subsequently, the control section 706 determines whether or not the intensity of brightness of the wavelength band measured by the spectrometer 703 is the set intensity (Step S203). In a case where the control section 706 determines that the intensity of brightness per wavelength band measured by the spectrometer 703 is the set intensity (Step S203: Yes), the adjustment apparatus 700 advances to later-described Step S205. In contrast, in a case where the control section 706 determines that the intensity of brightness per wavelength band measured by the spectrometer 703 is not the set intensity (Step S203: No), the adjustment apparatus 700 advances to later-described Step S204.

In Step S204, the control section 706 adjusts, on the basis of a difference between the intensity of brightness of the wavelength band measured by the spectrometer 703 and the set intensity, the current value at which the light source control section 33 causes the second light source section 32 to emit light and causes the second light source section 32 to emit light. After Step S204, the adjustment apparatus 700 returns to above-described Step S202.

In Step S205, the control section 706 generates the second calibration data, in which the current value to be supplied to the second light source section 32 by the light source control section 33, the emission time, and the intensity of brightness of wavelength band measured by the spectrometer 703 are associated with each other, and causes the calibration data record section 704a to record the second calibration data.

Subsequently, the control section 706 determines whether or not all the emission times settable for the second light source section 32 by the light source control section 33 have been completed (Step S206). In a case where the control section 706 determines that all the emission times settable for the second light source section 32 by the light source control section 33 have been completed (Step S206: Yes), the adjustment apparatus 700 returns to the main routine in FIG. 10, advancing to Step S3. In contrast, in a case where the control section 706 determines that all the emission times settable for the second light source section 32 by the light source control section 33 have not been completed (Step S206: No), the adjustment apparatus 700 advances to later-described Step S207.

In Step S207, the emission time for which the light source control section 33 causes the second light source section 32 to emit light is set at next one of the emission times and the second light source section 32 is caused to emit light. After Step S207, the adjustment apparatus 700 returns to above-described Step S202.

Referring back to FIG. 10, description will be continuously made on Step S3 and later.

In Step S3, the control section 706 causes the calibration data record section 351 of the light source apparatus 3 to record the calibration data recorded in the calibration data record section 704a. After Step S3, the adjustment apparatus 700 terminates the process.

FIG. 13 schematically illustrates an example of the calibration data generated by the adjustment apparatus 700 with use of the light source apparatus 3. As illustrated in FIG. 13, the first calibration data in which the current values (adjusted values), the emission times, and the emission intensities for the first light source section 31 are associated is recorded in calibration data G1. Further, the second calibration data in which the current values, the emission times, and the emission intensities for the second light source section 32 are associated is recorded in the calibration data G1. The adjustment apparatus 700 thus generates, for the unshipped light source apparatus 3 optically coupled thereto, the calibration data in which the current values (adjusted values), the emission times, and the emission intensities for each of the first light source section 31 and the second light source section 32 are associated and causes the calibration data record section 351 of the light source apparatus 3 to record the calibration data. In other words, at the time of adjustment, the adjustment apparatus 7 inputs the current value and the emission time and outputs the emission intensity. This allows the calibration data to be used by setting, according to a color balance ratio (for example, 1:P) between the first light source section 31 and the second light source section 32, the emission time sufficient for the emission intensity of the second light-emitting section 42 to be P×(the emission intensity of the first light-emitting section 31).

According to above-described Embodiment 4, the control section 706 generates, for the unshipped light source apparatus 3 optically coupled thereto, the calibration data in which the current values (adjusted values), the emission intensities, and the emission times for each of the first light source section 31 and the second light source section 32 are associated and causes the calibration data record section 351 of the light source apparatus 3 to record the calibration data. This makes it possible to adjust mismatching between the emission intensity and the current value of the light source apparatus 3.

Other Embodiments

A variety of inventions can be made by combining the plural components disclosed in the medical observation systems according to above-described Embodiments 1 to 3 of the present disclosure, if necessary. For example, out of all the described components in the medical observation systems according to above-described Embodiments 1 to 3 of the present disclosure, some components may be omitted. In addition, the explained components in the medical observation systems according to above-described Embodiments 1 to 3 of the present disclosure may be combined, if necessary.

In addition, in the medical observation systems according to Embodiments 1 to 3 of the present disclosure, the term "section" in the above description can be replaced with "means," "circuit," or the like. For example, the control section can be replaced with "control means" or "control circuit."

In addition, a program to be executed by the medical observation systems according to Embodiments 1 to 3 of the present disclosure is in the form of installable or executable file data and recorded in a computer-readable recording medium, such as a CD-ROM, a flexible disk (FD), a CD-R, a DVD (Digital Versatile Disk), a USB medium, or a flash memory, to be provided.

Alternatively, the program to be executed by the medical observation systems according to Embodiments 1 to 3 of the present disclosure may be stored on a computer connected to a network such as the Internet and downloaded through the network to be provided.

It should be noted that, in the description of the timing chart herein, the expressions such as "first," "after that," and "subsequently" are used to clarify a before-and-after relation of processing between timings; however, these expressions do not uniquely define an order of processing necessary for implementing the present disclosure. In other words, the order of processing in the timing chart described herein can be altered unless it leads to inconsistency.

Some of embodiments of the present application are described in detail with reference to the drawings hereinabove; however, these are exemplary and the present invention can be implemented not only in aspects described in the Disclosure of Invention section but also in any other form modified or improved in various manners on the basis of knowledge of be those skilled in the art.

It should be noted that the present technology can have the following configurations.

(Appendix 1)

A light source apparatus including:

a first light source section that is capable of pulse emission and emits a first light with which an object is to be irradiated;

a second light source section that is capable of pulse emission and emits a second light with which the object is to be irradiated; and a light source control section that controls each of a pulse emission time and a pulse emission intensity of the first light and performs a control that changes one of a pulse emission time and a pulse emission intensity of the second light with the other one of the pulse emission time and the pulse emission intensity of the second light fixed, in which, in the first light source section, a brightness of a captured image corresponding to an imaging signal generated as a result of an imaging device receiving light from the object irradiated with the first light with the pulse emission time and the pulse emission intensity of the first light maximized is higher than a brightness of a captured image corresponding to an imaging signal generated as a result of the imaging device receiving light from the object irradiated with the second light with the pulse emission time and the pulse emission intensity of the second light maximized.

(Appendix 2)

The light source apparatus according to Appendix 1, in which the first light source section generates, as the first light, light enabling white-color observation, and the second light source section generates, as the second light, light that excites a fluorescent substance.

(Appendix 3)

The light source apparatus according to Appendix 1 or 2, in which the light source control section performs a control that causes the first light source section and the second light source section to alternately emit the light and performs a control that changes the pulse emission time with the pulse emission intensity of the second light fixed during emission from the second light source section.

(Appendix 4)

A medical observation system including:

the light source apparatus according to any one of Appendices 1 to 3;

an imaging device that receives light from the object and generates an imaging signal; and an image processing section that generates, from the imaging signal generated by the imaging device, a display image to be displayed on a display section.

(Appendix 5)

An adjustment apparatus optically capable of coupling to the light source apparatus according to any one of Appendices 1 to 3, the adjustment apparatus including:

a measurement section that is able to measure an emission intensity of each of the first light and the second light; and a control section that causes the first light source section or the second light source section to emit light at a predetermined current value, in which the control section generates, based on a difference between a result of measurement by the measurement section and a preset emission intensity, calibration data in which an adjusted value provided by adjusting the current value and the preset emission intensity are associated with each other, and causes a memory of the light source apparatus to record the calibration data.

(Appendix 6)

An illumination method to be performed by a light source apparatus, the light source apparatus including a first light source section that is capable of pulse emission and emits a first light with which an object is to be irradiated, and a second light source section that is capable of pulse emission and emits a second light with which the object is to be irradiated, a brightness of a captured image corresponding to an imaging signal generated as a result of an imaging device receiving light from the object irradiated with the first light with a pulse emission time and a pulse emission intensity of the first light maximized being higher than a brightness of a captured image corresponding to an imaging signal generated as a result of the imaging device receiving light from the object irradiated with the second light with a pulse emission time and a pulse emission intensity of the second light maximized, the illumination method including:

controlling each of the pulse emission time and the pulse emission intensity of the first light; and changing one of the pulse emission time and the pulse emission intensity of the second light with the other one of the pulse emission time and the pulse emission intensity of the second light fixed.

(Appendix 7)

An adjustment method to be performed by an adjustment apparatus optically coupled to a light source apparatus, the light source apparatus including a first light source section that is capable of pulse emission and emits a first light with which an object is to be irradiated, and a second light source section that is capable of pulse emission and emits a second light with which the object is to be irradiated, a brightness of a captured image corresponding to an imaging signal generated as a result of an imaging device receiving light from the object irradiated with the first light with a pulse emission time and a pulse emission intensity of the first light maximized being higher than a brightness of a captured image corresponding to an imaging signal generated as a result of the imaging device receiving light from the object irradiated with the second light with a pulse emission time and a pulse emission intensity of the second light maximized, the adjustment method including:

measuring an emission intensity of each of the first light and the second light;

causing the first light source section or the second light source section to emit light at a predetermined current value;

generating, based on a difference between a result of the measuring of the emission intensity of each of the first light and the second light and a preset emission intensity, calibration data in which an adjusted value provided by adjusting the current value and the preset emission intensity are associated with each other; and causing a memory of the light source apparatus to record the calibration data.

(Appendix 8)

A program to be executed by a light source apparatus, the light source apparatus including a first light source section that is capable of pulse emission and emits a first light with which an object is to be irradiated, and a second light source section that is capable of pulse emission and emits a second light with which the object is to be irradiated, a brightness of a captured image corresponding to an imaging signal generated as a result of an imaging device receiving light from the object irradiated with the first light with a pulse emission time and a pulse emission intensity of the first light maximized being higher than a brightness of a captured image corresponding to an imaging signal generated as a result of the imaging device receiving light from the object irradiated with the second light with a pulse emission time and a pulse emission intensity of the second light maximized, the program including:

controlling each of the pulse emission time and the pulse emission intensity of the first light; and changing one of the pulse emission time and the pulse emission intensity of the second light with the other one of the pulse emission time and the pulse emission intensity of the second light fixed.

(Appendix 9)

A program to be executed by an adjustment apparatus optically coupled to a light source apparatus, the light source apparatus including a first light source section that is capable of pulse emission and emits a first light with which an object is to be irradiated, and a second light source section that is capable of pulse emission and emits a second light with which the object is to be irradiated, a brightness of a captured image corresponding to an imaging signal generated as a result of an imaging device receiving light from the object irradiated with the first light with a pulse emission time and a pulse emission intensity of the first light maximized being higher than a brightness of a captured image corresponding to an imaging signal generated as a result of the imaging device receiving light from the object irradiated with the second light with a pulse emission time and a pulse emission intensity of the second light maximized, the program including:

measuring an emission intensity of each of the first light and the second light;

causing the first light source section or the second light source section to emit light at a predetermined current value;

generating, based on a difference between a result of the measuring of the emission intensity of each of the first light and the second light and a preset emission intensity, calibration data in which an adjusted value provided by adjusting the current value and the preset emission intensity are associated with each other; and causing a memory of the light source apparatus to record the calibration data.

REFERENCE SIGNS LIST 1, 200: Endoscope system
2, 202: Insertion section
3, 210, 316: Light source apparatus
4: Light guide
5: Camera head
6: First transmission cable
7, 230, 311: Display apparatus
8: Second transmission cable
9, 220, 315: Control apparatus
10: Third transmission cable
21: Eyepiece section
31: First light source section
32: Second light source section
33: Light source control section
34, 701: Connector section
35, 97, 704: Memory
51: Manipulation ring section
52: Input section
61: First connector section
62: Second connector section 91: Signal processing section
92: Image processing section
93: Brightness detection section
94, 503, 705: Communication module
95: Input section
96: Output section
98, 706: Control section
200: Endoscope system
201: Endoscope
300: Surgical microscope system
310: Microscope apparatus
312: Microscope section
313: Support section
314: Base section
316: Light source apparatus
351, 704a, 971: Calibration data record section
501: Lens unit
502: Imaging section
504: Camera head control section
702: Integrating sphere
703: Spectrometer

The invention claimed is:

1. A light source apparatus comprising:
a first light source section that is capable of pulse emission and emits a first light with which an object is to be irradiated;
a second light source section that is capable of pulse emission and emits a second light with which the object is to be irradiated; and
a light source control section that controls each of a pulse emission time and a pulse emission intensity of the first light and performs a control that changes one of a pulse emission time and a pulse emission intensity of the second light with the other one of the pulse emission time and the pulse emission intensity of the second light fixed, wherein,
in the first light source section, a brightness of a captured image corresponding to an imaging signal generated as a result of an imaging device receiving light from the object irradiated with the first light with the pulse emission time and the pulse emission intensity of the first light maximized is higher than a brightness of a captured image corresponding to an imaging signal generated as a result of the imaging device receiving light from the object irradiated with the second light with the pulse emission time and the pulse emission intensity of the second light maximized.

2. The light source apparatus according to claim 1, wherein
the first light source section generates, as the first light, light enabling white-color observation, and
the second light source section generates, as the second light, light that excites a fluorescent substance.

3. The light source apparatus according to claim 2, wherein
the light source control section performs a control that causes the first light source section and the second light source section to alternately emit the light and performs a control that changes the pulse emission time with the pulse emission intensity of the second light fixed during emission from the second light source section.

4. A medical observation system comprising:
the light source apparatus according to claim 2;
an imaging device that receives light from the object and generates an imaging signal; and
an image processing section that generates, from the imaging signal generated by the imaging device, a display image to be displayed on a display section.

5. An adjustment apparatus optically capable of coupling to the light source apparatus according to claim 2, the adjustment apparatus comprising:
a measurement section that is able to measure an emission intensity of each of the first light and the second light; and
a control section that causes the first light source section or the second light source section to emit light at a predetermined current value, wherein
the control section
generates, based on a difference between a result of measurement by the measurement section and a preset emission intensity, calibration data in which an adjusted value provided by adjusting the current value and the preset emission intensity are associated with each other, and
causes a memory of the light source apparatus to record the calibration data.

6. The light source apparatus according to claim 1, wherein
the light source control section performs a control that causes the first light source section and the second light source section to alternately emit the light and performs a control that changes the pulse emission time with the pulse emission intensity of the second light fixed during emission from the second light source section.

7. A medical observation system comprising:
the light source apparatus according to claim 6;
an imaging device that receives light from the object and generates an imaging signal; and
an image processing section that generates, from the imaging signal generated by the imaging device, a display image to be displayed on a display section.

8. An adjustment apparatus optically capable of coupling to the light source apparatus according to claim 6, the adjustment apparatus comprising:
a measurement section that is able to measure an emission intensity of each of the first light and the second light; and
a control section that causes the first light source section or the second light source section to emit light at a predetermined current value, wherein
the control section
generates, based on a difference between a result of measurement by the measurement section and a preset emission intensity, calibration data in which an adjusted value provided by adjusting the current value and the preset emission intensity are associated with each other, and
causes a memory of the light source apparatus to record the calibration data.

9. A medical observation system comprising:
the light source apparatus according to claim 1;
an imaging device that receives light from the object and generates an imaging signal; and
an image processing section that generates, from the imaging signal generated by the imaging device, a display image to be displayed on a display section.

10. An adjustment apparatus optically capable of coupling to the light source apparatus according to claim 1, the adjustment apparatus comprising:
a measurement section that is able to measure an emission intensity of each of the first light and the second light; and a control section that causes the first light source section or the second light source section to emit light at a predetermined current value, wherein
the control section
generates, based on a difference between a result of measurement by the measurement section and a preset emission intensity, calibration data in which an adjusted value provided by adjusting the current value and the preset emission intensity are associated with each other, and
causes a memory of the light source apparatus to record the calibration data.

11. An illumination method to be performed by a light source apparatus, the light source apparatus including
a first light source section that is capable of pulse emission and emits a first light with which an object is to be irradiated, and
a second light source section that is capable of pulse emission and emits a second light with which the object is to be irradiated,
a brightness of a captured image corresponding to an imaging signal generated as a result of an imaging device receiving light from the object irradiated with the first light with a pulse emission time and a pulse emission intensity of the first light maximized being higher than a brightness of a captured image corresponding to an imaging signal generated as a result of the imaging device receiving light from the object irradiated with the second light with a pulse emission time and a pulse emission intensity of the second light maximized, the illumination method comprising:
controlling each of the pulse emission time and the pulse emission intensity of the first light; and
changing one of the pulse emission time and the pulse emission intensity of the second light with the other one of the pulse emission time and the pulse emission intensity of the second light fixed.

12. An adjustment method to be performed by an adjustment apparatus optically coupled to a light source apparatus, the light source apparatus including
a first light source section that is capable of pulse emission and emits a first light with which an object is to be irradiated, and
a second light source section that is capable of pulse emission and emits a second light with which the object is to be irradiated,
a brightness of a captured image corresponding to an imaging signal generated as a result of an imaging device receiving light from the object irradiated with the first light with a pulse emission time and a pulse emission intensity of the first light maximized being higher than a brightness of a captured image corresponding to an imaging signal generated as a result of the imaging device receiving light from the object irradiated with the second light with a pulse emission time and a pulse emission intensity of the second light maximized, the adjustment method comprising:
measuring an emission intensity of each of the first light and the second light;
causing the first light source section or the second light source section to emit light at a predetermined current value;
generating, based on a difference between a result of the measuring of the emission intensity of each of the first light and the second light and a preset emission intensity, calibration data in which an adjusted value provided by adjusting the current value and the preset emission intensity are associated with each other; and
causing a memory of the light source apparatus to record the calibration data.

13. A non-transitory computer-readable recording medium that stores a computer program to be executed by processing circuitry of a light source apparatus, the light source apparatus including
a first light source section that is capable of pulse emission and emits a first light with which an object is to be irradiated, and
a second light source section that is capable of pulse emission and emits a second light with which the object is to be irradiated,
a brightness of a captured image corresponding to an imaging signal generated as a result of an imaging device receiving light from the object irradiated with the first light with a pulse emission time and a pulse emission intensity of the first light maximized being higher than a brightness of a captured image corresponding to an imaging signal generated as a result of the imaging device receiving light from the object irradiated with the second light with a pulse emission time and a pulse emission intensity of the second light maximized, the processing circuitry is configured by execution of the program to implement a method comprising:
controlling each of the pulse emission time and the pulse emission intensity of the first light; and
changing one of the pulse emission time and the pulse emission intensity of the second light with the other one of the pulse emission time and the pulse emission intensity of the second light fixed.

14. A non-transitory computer-readable recording medium that stores a computer program to be executed by processing circuitry of an adjustment apparatus optically coupled to a light source apparatus, the light source apparatus including
a first light source section that is capable of pulse emission and emits a first light with which an object is to be irradiated, and
a second light source section that is capable of pulse emission and emits a second light with which the object is to be irradiated,
a brightness of a captured image corresponding to an imaging signal generated as a result of an imaging device receiving light from the object irradiated with the first light with a pulse emission time and a pulse emission intensity of the first light maximized being higher than a brightness of a captured image corresponding to an imaging signal generated as a result of the imaging device receiving light from the object irradiated with the second light with a pulse emission time and a pulse emission intensity of the second light maximized, the processing circuitry is configured by execution of the program to implement a method comprising:
measuring an emission intensity of each of the first light and the second light;
causing the first light source section or the second light source section to emit light at a predetermined current value;
generating, based on a difference between a result of the measuring of the emission intensity of each of the first light and the second light and a preset emission intensity, calibration data in which an adjusted value provided by adjusting the current value and the preset emission intensity are associated with each other; and causing a memory of the light source apparatus to record the calibration data.

* * * * *